(12) United States Patent
Roberts et al.

(10) Patent No.: US 6,498,196 B1
(45) Date of Patent: Dec. 24, 2002

(54) COMPOUNDS USEFUL IN PAIN MANAGEMENT

(76) Inventors: Edward Roberts, Höhenweg 12, 4112 Flüh (CH); Tiechao Li, 12853 Turnham Dr., Fishers, IN (US) 46038; Dilip Dixit, 72 Jean Brillant, Roxboro (CA), H8Y 2S5; Krzysztof Bednarski, 237 Labrie, Laval, Quebec (CA), H7N 5R6; Dick Storer, 215 Oakridge, Baie d'Urfe, Quebec (CA), H9X 2N3; Wuyi Wang, 2297 Frenette, Ville St-Laurent, Quebec (CA), H4R 1M3

( * ) Notice: Subject to any disclaimer, the term of this patent is extended or adjusted under 35 U.S.C. 154(b) by 0 days.

(21) Appl. No.: 09/460,722

(22) Filed: Dec. 14, 1999

Related U.S. Application Data

(60) Provisional application No. 60/113,542, filed on Dec. 22, 1998.

(51) Int. Cl.$^7$ .................. A61K 31/10; C07C 319/00
(52) U.S. Cl. ..................... 514/712; 568/18; 568/38; 568/58
(58) Field of Search .............. 568/38, 18, 58; 514/712

(56) References Cited

U.S. PATENT DOCUMENTS 5,545,755 A * 8/1996 Lin et al. ............... 564/428

FOREIGN PATENT DOCUMENTS

| GB | 1 377 356 | 12/1974 | ........... C07C/91/46 |
| GB | 1377356 | * 12/1974 | |
| WO | WO 91/09006 | 6/1991 | ......... C07C/215/64 |
| WO | WO 95/04028 | 2/1995 | ......... C07C/211/53 |
| WO | WO 97/16422 | 5/1997 | ......... C07C/323/62 |

OTHER PUBLICATIONS

Martin, et al., "The Effects of Morphine– and Nalorphine–Like Drugs in the Nondependent and Morphine–Dependent Chronic Spinal Dog," *J. Pharmacol. Exper. Therap.* 197(3):517–532 (1976).

Takeda, et al., "1,1–Dimethyl–2–dimethylamino–7–hydroxy–1,2,3,4–tetrahydronaphthalene," STN International File CAPLUS, CAPLUS, Acc. No. 1973:546294, Doc. No. 79:146294.

Hirose, et al., "Synthesis and Analgesic Activities of Some 2–amino–1,1–dialkyl–7–methoxy–1,2,3,4–tetrahydronaphthalenes and Related Compounds," STN Intenational File, CAPLUS, CAPLUS Acc. No. 1976:542882, Doc. No. 85:142882.

Krotowska, et al., "Dopamine D2–Receptor Affinities of Resolved C1–dimethylated 2–aminotetralins," STN International File CAPLUS, CAPLUS Acc. No. 1988:87584, Doc. No. 108:87584.

Lord, et al., "Endogenous Opioid Peptides: Multiple Agonists and Receptors," *Nature* 267:495–499 (1977).

Budd, "Analgesic Drugs," *International Encyclopedia of Pharmacology and Therapeutics*, N.E. Williams and H. Wilkinson, Eds., Pergammon: (Oxford) 51–63 (1983).

Hacksell, et al., "C1–Methylated 5–hydroxy–2–(dipropylamino) tetralins: Central Dopamine–Receptor Stimulating Activity," STN International File CAPLUS, CAPLUS Acc. No. 1984:454672, Doc. No. 101:54672.

Hirose, et al., "Hydroxytetrahydronaphthalene Derivatives," Abstract No. 43700e, *Chemical Abstracts 84(7)*:458 (1976).

* cited by examiner

Primary Examiner—Mukund J. Shah
Assistant Examiner—Sudhaker B. Patel
(74) Attorney, Agent, or Firm—Michael A. Sanzo; Fitch, Even, Tabin & Flannery

(57) ABSTRACT

The present invention relates to novel thio-aminotetralin compounds of the formula (I)

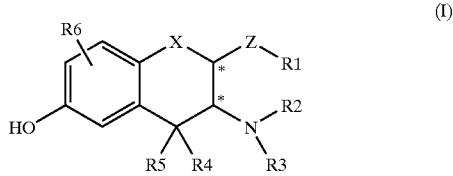

(I)

wherein Z, X, $R_1$, $R_2$, $R_3$, $R_4$, $R_5$, and $R_6$ are defined herein. The compounds are useful in pain management.

24 Claims, No Drawings

COMPOUNDS USEFUL IN PAIN MANAGEMENT

CROSS REFERENCE TO RELATED APPLICATIONS

The present application claims the benefit of U.S. provisional application No. 60/113,542, filed on Dec. 22, 1998.

FIELD OF THE INVENTION

The present invention is related to compounds that exhibit analgesic activity and in particular compounds exhibiting analgesia due to their opioid receptor affinity.

BACKGROUND OF THE INVENTION

Many natural alkaloids and related analogs bind to specific opioid receptors and elicit an analgesic response similar to classic narcotic opiates. Many different types of opioid receptors have been shown to coexist in higher animals. For example, see W. Martin et al., *J. Pharmacol. Exp. Ther* 197, p. 517 (1975); and J. Lord et al., *Nature* (London), 257, p.495 (1977). Three different types of opioid receptors have been identified. The first, δ, shows a differentiating affinity for enkephalin-like peptides. The second, μ, shows enhanced selectivity for morphine and other polycyclic alkaloids. The third, κ, exhibits equal affinity for either group of the above ligands and preferential affinity for dynorphin. In general, the μ receptors seem to be more involved with analgesic effects. The δ receptors appear to deal with behavioral effects, although the δ and the κ receptors may also mediate analgesia.

Each opioid receptor, when coupled with an opiate, causes a specific biological response unique to that type of receptor. When an opiate activates more than one receptor, the biological response for each receptor is affected, thereby producing side effects. The less specific and selective an opiate may be, the greater the chance of causing increased side effects by the administration of the opiate.

Opiates can cause serious and potentially fatal side effects. Side effects such as respiratory depression, tolerance, physical dependence capacity, and precipitated withdrawal syndrome are caused by nonspecific interactions with central nervous system receptors. See K. Budd, In *International Encyclopedia of Pharmacology and Therapeutics;* N. E. Williams and H. Wilkinson, Eds., Pergammon: (Oxford), 112, p.51 (1983). It is therefore an object of the present invention to provide compounds having analgesic effects but having as few side-effects as possible.

DESCRIPTION OF THE INVENTION

In one aspect, the present invention provides novel thio aminotetralin compounds represented by formula (I):

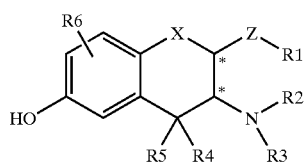

(I)

and pharmaceutically acceptable derivatives thereof; wherein;

Z is S, SO or $SO_2$,

X is selected from anyone of (i) a bond;
(ii) —$CR_7R_8$— wherein $R_7$ and $R_8$ are independently selected from the group consisting of H, OH, halogen, CN, COOH, $CONH_2$, amino, nitro, SH, $C_{1-6}$ alkyl where one or more of the carbon atoms may optionally be substituted by one or more heteroatoms selected from O, S and N, $C_{2-6}$alkenyl where one or more of the carbon atoms may optionally be substituted by one or more heteroatoms selected from O, S and N, $C_{2-6}$alkynyl where one or more of the carbon atoms may optionally be substituted by one or more heteroatoms selected from O, S and N; and $COOR_C$ wherein $R_c$ is $C_{1-6}$alkyl, $C_{2-6}$alkenyl or $C_{2-6}$alkynyl; $R_7$ and $R_8$ can also be connected to form $C_{3-8}$ cycloalkyl, a $C_{3-8}$ cycloalkenyl or a saturated heterocycle of from 3 to 8 atoms;

$R_1$ is selected from the group consisting of H, $C_{1-12}$alkyl where one or more of the carbon atoms may optionally be substituted by one or more heteroatoms selected from O, S and N, $C_{2-12}$alkenyl where one or more of the carbon atoms may optionally be substituted by one or more heteroatoms selected from O, S and N, $C_{2-12}$alkynyl where one or more of the carbon atoms may optionally be substituted by one or more heteroatoms selected from O, S and N, $C_{6-12}$ aryl, $C_{6-12}$ aralkyl, $C_{6-12}$ aryloxy, $C_{1-12}$ acyl, heteroaryl having from 6 to 12 atoms, and phosphoryl;

$R_2$ and $R_3$ are independently selected from the group consisting of $C_{1-6}$ alkyl where one or more of the carbon atoms may optionally be substituted by one or more heteroatoms selected from O, S and N, $C_{2-6}$alkenyl where one or more of the carbon atoms may optionally be substituted by one or more heteroatoms selected from O, S and N, $C_{2-6}$alkynyl where one or more of the carbon atoms may optionally be substituted by one or more heteroatoms selected from O, S and N, $C_{6-12}$ aryl, $C_{6-12}$ aralkyl, heteroaryl having from 6 to 12 atoms, and H; or $R_2$ and $R_3$ may together form a saturated heterocycle of from 3 to 8 atoms;

$R_4$ and $R_5$ are independently selected from the group consisting of $C_{1-6}$ alkyl where one or more of the carbon atoms may optionally be substituted by one or more heteroatoms selected from O, S and N, $C_{2-6}$alkenyl where one or more of the carbon atoms may optionally be substituted by one or more heteroatoms selected from O, S and N, $C_{2-6}$alkynyl where one or more of the carbon atoms may optionally be substituted by one or more heteroatoms selected from O, S and N, and H;

$R_4$ and $R_5$ can also be connected to form $C_{3-8}$ cycloalkyl, a $C_{3-8}$ cycloalkenyl or a saturated heterocycle of from 3 to 8 atoms;

$R_6$ is hydrogen, OH, $C_{1-6}$ alkyl where one or more of the carbon atoms may optionally be substituted by one or more heteroatoms selected from O, S and N, $C_{2-6}$alkenyl where one or more of the carbon atoms may optionally be substituted by one or more heteroatoms selected from O, S and N, $C_{2-6}$alkynyl where one or more of the carbon atoms may optionally be substituted by one or more heteroatoms selected from O, S and N, O—$C_{1-6}$ alkyl where one or more of the carbon atoms may optionally be substituted by one or more heteroatoms selected from O, S and N, O—$C_{2-6}$alkenyl where one or more of the carbon atoms may optionally be substituted by one or more heteroatoms selected from O, S and N, O—$C_{2-6}$alkynyl where one or more of the carbon atoms may optionally be substituted by one or more heteroatoms selected from O, S and N, halogen, CN, COOH, CONH$_2$, amino, nitro, or SH;

with the provisos that:
1) not both $R_4$ and $R_5$ are H; and
2) at least one of $R_2$ and $R_3$ is H or $C_{1-6}$ alkyl.

The compounds of the present invention are useful in therapy, in particular as analgesics.

In another aspect, there is provided a method of treating pain in a mammal, comprising administering to said mammal an analgesic amount of a compound or composition of the invention.

Still another aspect of the invention is the use of a compound according to formula (I), for the manufacture of a medicament for the treatment of pain.

In another aspect, there is provided pharmaceutical compositions comprising compounds of the present invention and pharmaceutically acceptable carriers, diluents or adjuvants.

X is preferably —$CR_7R_8$— wherein $R_7$ and $R_8$ are independently selected from the group consisting of OH, halogen, CN, COOH, CONH$_2$, amino, nitro, SH, $C_{1-6}$ alkyl where one or more of the carbon atoms may optionally be substituted by one or more heteroatoms selected from O, S and N, H, and COOR$_c$ wherein R$_c$ is $C_{1-6}$alkyl; $R_7$ and $R_8$ can also be connected to form a $C_{3-8}$ cycloalkyl.

X is more preferably —$CR_7R_8$— wherein $R_7$ and $R_8$ are independently selected from the group consisting of $C_{1-6}$ alkyl, and H.

X is most preferably —CH$_2$—.

$R_1$ is preferably selected from the group consisting of H, $C_{1-12}$alkyl, $C_{6-12}$ aryl, and $C_{6-12}$ aralkyl.

$R_1$ is more preferably selected from the group consisting of $C_{1-6}$alkyl, $C_{6-12}$ aryl, and $C_{6-12}$ aralkyl.

$R_1$ is most preferably $C_{1-6}$ alkyl.

$R_1$ can also be

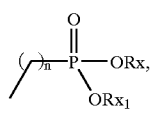

wherein n is an integer between 1 to 5, Rx and Rx$_1$ are independently H, $C_{1-6}$alkyl, $C_{2-6}$alkenyl or $C_{2-6}$alkynyl. More preferably, n is 1 or 2 and Rx and Rx$_1$ are $C_{1-6}$alkyl. Most preferably, Rx and Rx$_1$ are methyl or ethyl.

In an alternative embodiment, $R_1$ is selected from the group consisting of CH$_3$, —(CH$_2$)$_n$—CH$_3$, and —(CH$_2$)$_n$—O—CH$_3$ wherein n is an integer selected between 1 and 5. In an alternative preferred embodiment $R_1$ is $C_{6-12}$ aryl or heteroaryl having from 6 to 12 atoms.

In a further preferred embodiment, $R_1$ is selected from the group consisting of

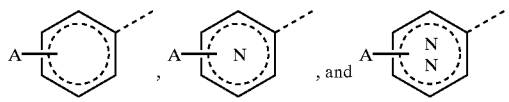

wherein A is selected from the group consisting of $C_{1-6}$ alkyl, $C_{1-6}$alkyl, $C_{2-6}$alkenyl, $C_{2-6}$alkynyl, O—$C_{1-6}$ alkyl, O—$C_{2-6}$alkenyl, O—$C_{2-6}$alkynyl, S—$C_{1-6}$ alkyl, S—$C_{2-6}$alkenyl, S—$C_{2-6}$alkynyl, N—$C_{1-6}$ alkyl, N—$C_{2-6}$alkenyl, N—$C_{2-6}$alkynyl, CF$_3$, fluoro, chloro, bromo, iodo, OH, SH, CN, nitro, amino, aminoamidino, amidino, guanido, COOH, and COOR$_z$ wherein R$_z$ is $C_{1-6}$alkyl, $C_{2-6}$alkenyl or $C_{2-6}$alkynyl.

In an alternative embodiment, $R_1$ is $C_{6-12}$ aralkyl or heteroaryl having from 6 to 12 atoms.

More preferably, $R_1$ is selected from the group consisting of

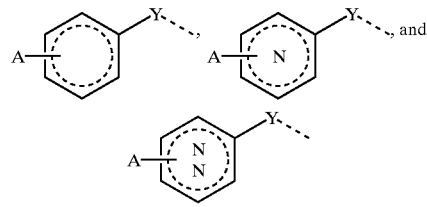

wherein A is selected from the group consisting of $C_{1-6}$ alkyl, $C_{1-6}$alkyl, $C_{2-6}$alkenyl, $C_{2-6}$alkynyl, O—$C_{1-6}$ alkyl, O—$C_{2-6}$alkenyl, O—$C_{2-6}$alkynyl, S—$C_{1-6}$ alkyl, S—$C_{2-6}$alkenyl, S—$C_{2-6}$alkynyl, N—$C_{1-6}$ alkyl, N—$C_{2-6}$alkenyl, N—$C_{2-6}$alkynyl, CF$_3$, fluoro, chloro, bromo, iodo, OH, SH, CN, nitro, amino, aminoamidino, amidino, guanido, COOH, and COOR$_z$ wherein R$_z$ is $C_{1-6}$alkyl, $C_{2-6}$alkenyl or $C_{2-6}$alkynyl and Y is —(CH$_2$)$_m$— wherein m is an integer selected between 1 and 5.

$R_1$ is preferably

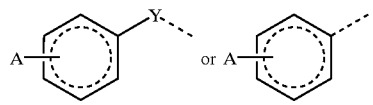

wherein A and Y are as defined above.

A is preferably selected from the group consisting of $C_{1-6}$ alkyl, O—$C_{1-6}$ alkyl, S—$C_{1-6}$ alkyl, OH, nitro, amino, aminoamidino, amidino, guanido, COOH, and COOR$_a$ wherein R$_a$ is $C_{1-6}$alkyl, $C_{2-6}$alkenyl or $C_{2-6}$alkynyl. A is more preferably selected from the group consisting of $C_{1-6}$ alkyl, OH, nitro, amino, aminoamidino, amidino, guanido, and COOH. A is most preferably selected from the group consisting of amidino, guanido, and OH.

$R_2$ and $R_3$ are preferably H.

$R_4$ and $R_5$ are preferably $C_{1-4}$ alkyl substituted by a hydroxyl.

$R_4$ and $R_5$ are preferably $C_{1-4}$ alkyl.

In a further preferred embodiment, $R_4$ and $R_5$ are independently selected from the group consisting of methyl, ethyl, isopropyl, propyl, butyl, and isobutyl.

$R_4$ and $R_5$ are preferably ethyl.

$R_4$ and $R_5$ are preferably methyl.

$R_6$ can be substituted at any position on the aromatic ring. More preferably $R_6$ is adjacent to the carbon bearing the OH. In an alternative embodiment, the present invention provides compounds of the formula (II) or (III)

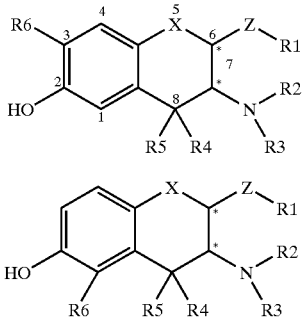

(II)

(III)

and pharmaceutically acceptable derivative;
wherein each of X, Z, $R_1$, $R_2$, $R_3$, $R_4$, $R_5$, and $R_6$ are defined above.

$R_6$ is preferably, H, methyl, halogen or $OR_b$ wherein $R_b$ is $C_{1-6}$alkyl, $C_{1-6}$alkenyl or $C_{1-6}$alkynyl.

$R_6$ is most preferably H.

The compounds of the present invention contains at least 2 chiral centers which are marked by an asterik (*) on the general formula (I). The compounds of formula (I) thus exist in the form of different geometric (i.e. trans and cis) and optical isomers (i.e. (+) or (−) enantiomers). When there is 2 chiral centers at the position marked by the asteriks, the compounds may therefore be in the form of cis isomers or trans isomers. Each cis or trans isomers also exists as a (+) and (−) enantiomer. All such isomers, enantiomers and mixtures thereof including racemic mixtures are included within the scope of the invention.

Preferably the compounds of the present invention are in the form of the trans isomers. More preferably the compounds of the present invention are present in the form of trans (+) and trans (−) enantiomers.

Preferred compounds of the invention include:Trans-7-Amino-8,8-dimethyl-6-methylsulfanyl-5,6,7,8-dihydro-naphthalen-2-ol (compound #1);Cis-7-Amino-8,8-dimethyl-6-methylsulfanyl-5,6,7,8-dihydro-naphthalen-2-ol (compound #2); Trans-7-Amino-8,8-diethyl-6-methylsulfanyl-5,6,7,8-dihydro-naphthalen-2-ol (compound #3);Trans-7-Amino-8,8-dimethyl-6-phenylsulfanyl-5,6,7,8-tetrahydro-naphthalen-2-ol (compound #4);
Trans-7-Amino-8,8-dimethyl-6-(pyridin-2-ylsulfanyl)-5,6,7,8-tetrahydro-naphthalen-2-ol (Compound #5);
Trans-7-Amino-8,8-dimethyl-6-(pyrimidin-2-ylsulfanyl)-5,6,7,8-tetrahydro-naphthalen-2-ol (Compound #6);
Trans-7-Amino-6-(3-amino-phenylsulfanyl)-8,8-dimethyl-5,6,7,8-tetrahydro-naphthalen-2-ol (Compound #7);
Trans-7-Amino-8,8-dimethyl-6-(4-methylsulfanyl-phenylsulfanyl)-5,6,7,8-tetrahydro-naphthalen-2-ol (Compound #8);
Trans-7-Amino-6-benzenesulfonylmethylsulfanyl-8,8-diethyl-5,6,7,8-tetrahydro-naphthalen-2-ol (Compound #9);
Trans-2-(3-Amino-4,4-diethyl-6-hydroxy-1,2,3,4-tetrahydro-naphthalen-2-ylsulfanyl)-acetamide (Compound #10);
Trans-(3-Amino-4,4-diethyl-6-hydroxy-1,2,3,4-tetrahydro-naphthalen-2-ylsulfanylmethyl)-phosphonic acid diethyl ester (Compound #11);
Trans-7-Amino-8,8-diethyl-6-(2-hydroxy-ethylsulfanyl)-5,6,7,8-tetrahydro-naphthalen-2-ol (Compound #12);
Trans-7-Amino-6-(5-amino-2H-[1,2,4]triazol-3-ylsulfanyl)-8,8-diethyl-5,6,7,8-tetrahydro-naphthalen-2-ol (Compound #13);
Trans-7-Amino-6-(2-amino-ethylsulfanyl)-8,8-dimethyl-5,6,7,8-tetrahydro-naphthalen-2-ol (Compound #14);
Trans-7-Amino-6-(5-amino-2H-[1,2,4]triazol-3-ylsulfanyl)-8,8-dimethyl-5,6,7,8-tetrahydro-naphthalen-2-ol (Compound #15);
Trans-7-Amino-8,8-dimethyl-6-propylsulfanyl-5,6,7,8-tetrahydro-naphthalen-2-ol (Compound #16);
Trans-7-Amino-6-isopropylsulfanyl-8,8-dimethyl-5,6,7,8-tetrahydro-naphthalen-2-ol (Compound #17);
Trans-7-Amino-6-(2-hydroxy-ethylsulfanyl)-8,8-dimethyl-5,6,7,8-tetrahydro-naphthalen-2-ol (Compound #18);
Trans-2-(3-Amino-6-hydroxy-4,4-dimethyl-1,2,3,4-tetrahydro-naphthalen-2-ylsulfanyl)-acetamide (Compound #19);
Trans-7-Dimethylamino-8,8-dimethyl-6-methylsulfanyl-5,6,7,8-tetrahydro-naphthalen-2-ol (Compound #20);
8,8-dimethyl-trans-7-methylamino-6methylsulfanyl-5,6,7,8-tetrahydro-naphthalen-2-ol (Compound #21);
Trans-7-Amino-8,8-diethyl-6-phenylsulfanyl-5,6,7,8-tetrahydro-naphthalen-2-ol (Compound #22);
8,8-dimethyl-trans-6-phenylsulfanyl-7-propylamino-5,6,7,8-tetrahydro-naphthalen-2-ol (Compound #23);
Trans-7-Amino-6-(2-amino-phenylsulfanyl)-8,8-diethyl-5,6,7,8-tetrahydro-naphthalen-2-ol (Compound #24;
Trans-7-Amino-8,8-dimethyl-6-(2,2,2-trifluoro-ethylsulfanyl)-5,6,7,8-tetrahydro-naphthalen-2-ol Compound #25);
Trans4-(3-Amino-6-hydroxy-4,4-dimethyl-1,2,3,4-tetrahydro-naphthalen-2-ylsulfanyl)-butyric acid ethyl ester (Compound #26);
Trans-7-Amino-6-benzenesulfonylmethylsulfanyl-8,8-dimethyl-5,6,7,8-tetrahydro-naphthalen-2-ol (Compound #27);
Trans-7-Amino-8,8-dimethyl-6-(3-phenyl-allylsulfanyl)-5,6,7,8-tetrahydro-naphthalen-2-ol (Compound #28);
Trans-7-Amino-6-isobutylsulfanyl-8,8-dimethyl-5,6,7,8-tetrahydro-naphthalen-2-ol (Compound #29);
Trans-7-Amino-8,8-dimethyl-6-(2-phenoxy-ethylsulfanyl)-5,6,7,8-tetrahydro-naphthalen-2-ol (Compound #30);
Trans-7-Amino-8,8-diethyl-6-(2-phenoxy-ethylsulfanyl)-5,6,7,8-tetrahydro-naphthalen-2-ol (Compound #31);
(−)Trans-7-amino-8,8-dimethyl-6-methylsulfanyl-5,66,7,8-tetrahydro-naphthalen-2-ol (Compound #32);
(+)Trans-7-amino-8,8-dimethyl-6-methylsulfanyl-5,6,7,8-tetrahydro-naphthalen-2-ol (Compound #33);Trans-7-amino-6-(4-bromo-phenylsulfanyl)-8,8-dimethyl-5,6,7,8-tetrahydronaphthalen-2-ol (Compound #34);
Trans-7-amino-8,8-dimethyl-6-(naphthalen-2-ylsulfanyl)-5,6,7,8-tetrahydro-naphthalen-2-ol (Compound #35);Trans7-Amino-6-(4-hydroxy-phenylsulfanyl)-8,8-dimethyl-5,6,7,8-tetrahydro-naphthalen-2-ol (Compound #36);Trans-7-amino-6-(4amino-phenylsulfanyl)-8,8-dimethyl-5,6,7,8-tetrahydro-naphthalen-2-ol (Compound #37);Trans-7-amino-6-(3-hydroxy-phenylsulfanyl)-8,8-dimethyl-5,6,7,8-tetrahydro-naphthalen-2-ol (Compound #38);Trans-3-(3-Amino-6-hydroxy-4,4-dimethyl-1,2,3,4-tetrahydro-naphthalen-2-ylsulfanyl)-propionic acid ethyl ester (Compound #39);Trans-7-amino-8,8-dimethyl-6-phenethylsulfanyl-5,6,7,8-tetrahydronaphthalen-2-ol (Compound #40);Trans-2-(3-amino-6-hydroxy-4,4-dimethyl 1,2,3,4-tetrahydronaphthalen-2-ylsulfanyl)- propionamide (Compound #41);Trans-3-(3-amino-6-hydroxy-4,4-dimethyl-1,2,3,4-tetrahydro-naphthalen-2-ylsulfanyl)-propionic acid (Compound #42);Trans-2-[3-(3-Amino-6-hydroxy-4,4-dimethyl-1,2,3,4-tetrahydro-naphthalen-2-ylsulfanyl)-propionylamino]-3-(4-hydroxy-phenyl)-propionamide (Compound #43); 3-trans-(2-ethoxycarbonyl-ethylsulfanyl)-1,1-diethyl-7-hydroxy-1,2,3,4-tetrahydro-naphthalen-2-yl (Compound #44); 3-trans-(2-carboxy-ethylsulfanyl)-1,1-diethyl-7-hydroxy-1,2,3,4-tetrahydro-naphthalen-2-yl (Compound #45); and pharmaceutically acceptable derivatives thereof; wherein said compound is in the form of the (+) enantiomer, the (−) enantiomer and mixture of the (+) and (−) enantiomer including racemic mixture.

More preferably the compound of the present invention is selected from the group consisting of compound#1, compound#3, compound#4, compound#5, compound#9, compound#11, compound#15, compound#31, compound#32, compound#33, compound#36, compound#37, compound#39 compound#41, compound#43, compound#44 and compound #45.

Most preferably the compound of the present invention is selected from the group consisting of compound#1, compound#3, compound#5, compound#32, compound#33, compound#36, compound#44 and compound#45.

As used in the present application the term "pain" represents "an unpleasant sensory and emotional experience associated with actual or potential tissue damage or described in terms of such damage. The term "pain" also includes "acute pain" and chronic pain.

Acute pain is usually immediate and of a short duration. Acute pain can be present further to an injury, short-term illness, or surgical/medical procedure.

Examples of acute pain include a burn, a fracture, an overused muscle, or pain after surgery. Cancer pain may be long-lasting but acute due to ongoing tissue damage.

Some chronic pain is due to damage or injury to nerve fibers themselves (neuropathic pain).

Chronic pain can result from diseases, such as shingles and diabetes, or from trauma, surgery or amputation (phantom pain). It can also occur without a known injury or disease.

The present invention s directed to the treatment of all type of pain, including acute and chronic pain.

As used in this application, the term "alkyl" represents an unsubstituted or substituted (by a halogen, nitro, aminoamidino, amidino, guanido, $CONH_2$, COOH, $O-C_{1-6}$ alkyl, $O-C_{2-6}$ alkenyl, $O-C_{2-6}$ alkynyl, amino, hydroxyl or COOQ, wherein Q is $C_{1-6}$ alkyl, $C_{2-6}$ alkenyl, a $C_{2-6}$ alkynyl) straight chain, branched chain, or cyclic hydrocarbon moiety (e.g. isopropyl, ethyl, flurohexyl or cyclopropyl). The term alkyl is also meant to include alkyls in which one or more hydrogen atoms is replaced by an halogen, more preferably, the halogen is fluoro (e.g., $CF_3—$, or $CF_3CH_2—$).

The term "saturated heterocycle" represents a carbocyclic ring in which one or more of the from 3 to 8 atoms of the ring are elements other than carbon, such as N, S and O;

The term "aryl" represents an aromatic ring having from 6 to 12 carbon atoms, which may be substituted by a $C_{1-6}$ alkyl, $C_{2-6}$ alkenyl, a $C_{2-6}$ alkynyl, halogen, nitro, aminoamidino, amidino, guanido, $CONH_2$, COOH, $O-C_{1-6}$ alkyl, $O-C_{2-6}$ alkenyl, $O-C_{2-6}$ alkynyl, amino, hydroxyl or COOQ, wherein Q is $C_{1-6}$ alkyl, $C_{2-6}$ alkenyl, a $C_{2-6}$ alkynyl, such as phenyl and naphthyl.

The term "aralkyl" represents an aryl group attached to the adjacent atom by a $C_{1-6}$alkyl, $C_{1-6}$alkenyl, or $C_{1-6}$alkynyl (e.g., benzyl).

The term "aryloxy" represents an aryl or aralkyl moiety covalently bonded through an oxygen atom (e.g., phenoxy).

The term "heteroaryl" represents an aromatic ring in which one or more of the from 6 to 12 atoms in the ring are elements other than carbon, such as O, N, and S (e.g pyridine, isoquinoline, or benzothiophene).

The term "acyl" refers to a radical derived from a carboxylic acid, substituted (by halogen(F, Cl, Br, I), $C_{6-20}$ aryl or $C_{1-6}$ alkyl) or unsubstituted, by replacement of the OH group. Like the acid to which it is related, an acyl radical may be aliphatic or aromatic, substituted (by halogen, $C_{1-5}$ alkoxyalkyl, nitro or OH) or unsubstituted, and whatever the structure of the rest of the molecule may be, the properties of the functional group remain essentially the same (e.g., acetyl, propionyl, isobutanoyl, pivaloyl, hexanoyl, trifluoroacetyl, chloroacetyl, and cyclohexanoyl).

The term "phosphoryl" represents a radical derived from a phosphono moeity in which the hydrogen atom of at least one of the —OH can be replaced by $C_{1-6}$ alkyl, $C_{2-6}$alkenyl, $C_{2-6}$alkynyl, $C_{1-6}$heteroalkyl, $C_{6-12}$ aryl, $C_{6-12}$ aralkyl, and $C_{6-12}$ heteroaryl(e.g., diethoxyphosphorylmethyl).

The term "halogen" encompasses chloro, fluoro, bromo and iodo;

In the present application the following abbreviations are used:

| | |
|---|---|
| AcOEt | ethyl acetate |
| Boc | t-butyloxycarbonyl |
| DMAP | 4-dimethylaminopyridine |
| DME | ethylene glycol dimethylether |
| DMF | dimethylformamide |
| $Et_2O$ | ether |
| Hex | hexane |
| HPLC | high performance liquid chromatography |
| LAH | lithium aluminium hydride |
| LHMDS | lithium bis(trimethylsilyl)amide |
| NHMDS | sodium bis(trimethylsilyl)amide |
| Ph | phenyl |
| PPTS | pyridium p-toluenesulfonate |
| PTSA | p-toluenesulfonic acid |
| r.t. | room temperature |
| sat. | saturated |
| TFA | trifluoroacetic acid |
| THF | tetrahydrofuran |
| TLC | thin layer chromatography |

When there is a sulfur atom present, the sulfur atom can be at different oxydation level, S, SO, or $SO_2$. All such oxydation level are within the scope of the present invention.

In yet another aspect of the invention, there is provided a process for preparing compounds of formula (I). The process is described in scheme 1 wherein each of X, $R_1$, $R_2$, $R_3$, $R_4$, $R_5$ and $R_6$ are as defined above and P, P1, P2, and P3 are protecting groups. If desired, the sulfur of the compound of formula Ia can be oxydized to S=O or $SO_2$ by methods well known in the art.

SCHEME 1

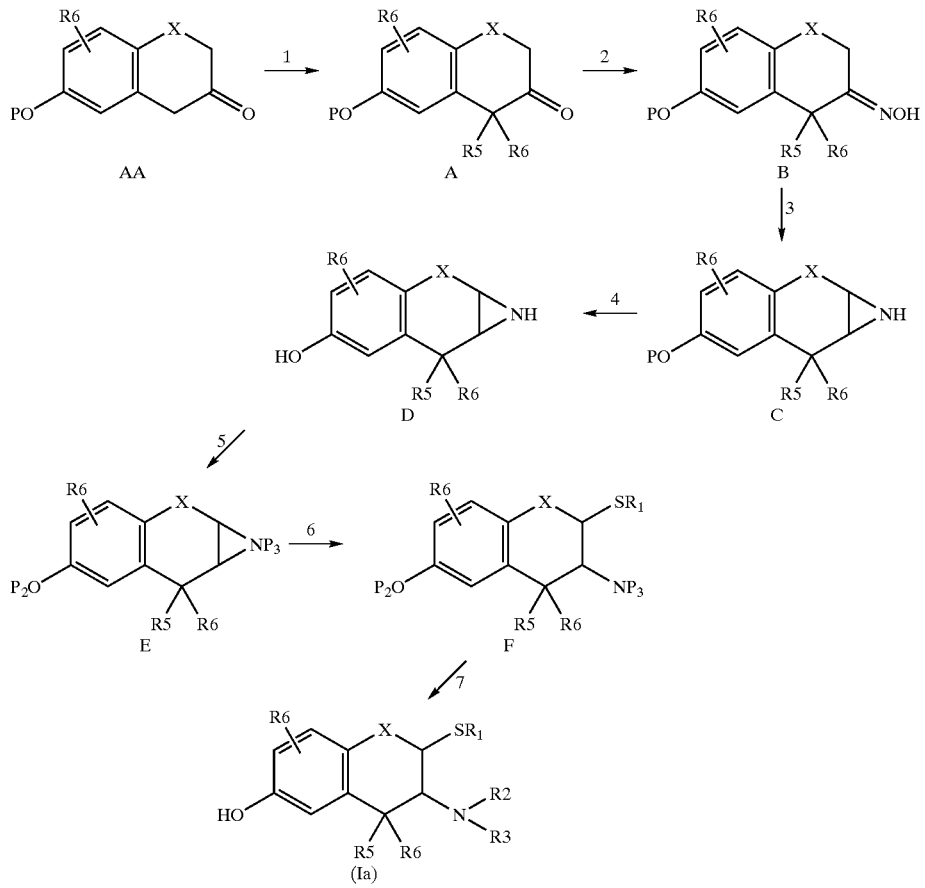

Step 1
The starting ketone AA was dissolved in a suitable solvent such as DMF, acetonitrile, THF, DME and was treated with sodium hydride or any other base such as potassium t-butoxide, sodium bis(trimethylsilyl)amide. The resulting mixture was then treated with ethyl iodide or any other alkyl halide such as methyl iodide, allyl bromide, diiodobutane to produce the compound A.

Step 2
The compound A was dissolved in a suitable solvent such as pyridine, DMF, ethanol and was treated with hydroxylamine hydrochloride or any other hydroxylamine salt such as hydroxylamine sulfate, hydroxylamine bromide to produce the compound B.

Step 3
The compound B was dissolved in a suitable solvent as THF, dioxane, DME, and was treated with LAH or any other reducing agent such as red-Al in presence of diethylamine or any other amine such as methylbutylamine, dipropylamine. The mixture was then heated to 50° C. or at any higher temperature to produce the compound C.

Step 4
The compound C in was dissolved in a suitable solvent as dichloromethane ($CH_2Cl_2$) or in any other solvent such as dichloroethane, and was treated with $BBr_3$ or any other demethylating agent such as $BCl_3$, HBr, to produce the compound D.

Step 5
The amino or hydroxyl groups of the compound D were protected with Boc or with any other protecting group, to produce the compound E. Protective groups are described in *Protective Groups in Organic Synthesis,* 2nd ed., Greene and Wuts, John Wiley & Sons, New York, 1991 which is herein incorparated by reference.

Step 6
The compound E was dissolved in a suitable solvent such as ethanol or in any other alcohol such as methanol, propanol, butanol and was treated with pyridinium p-toluenesulfonate (PPTS) or any other acid or Lewis acid such as HCl, $BF_3.OEt_2$, PTSA, to produce the compound F. Alternatively, a non alcoholic solvent can be used in combination with an appropriate amount of an alcohol and a suitable Lewis acid such as ytterbium triflate see for example *Tetrahedron Letters,* Vol. 37, No.43, pp7717–7720, 1996 which is herein incorparated by reference.

Step 7
The protecting groups of the compound F were removed under appropriate conditions e.g. with TFA or with any other acid such as HCl, PTSA, to produce the compound Ia.

It will be appreciated that certain substituents require protection during the course of the synthesis and subsequent deprotection. For example, it may be necessary to protect an hydroxyl group by converion to an alkoxy or an ester and subsequently deprotected. Protective groups for other substituents are described in *Protective Groups in Organic Synthesis,* 2nd ed., Greene and Wuts, John Wiley & Sons, New York, 1991.

In another aspect, there is provided a method of agonizing or activating opioid receptors in a mammal comprising administering to said mammal an opioid receptor agonizing or activating amount of a compound or composition of the invention.

There is also provided pharmaceutically acceptable compositions comprising compounds of the present invention and derivatives thereof, in combination with pharmaceutically acceptable carriers diluents or adjuvants.

By "pharmaceutically acceptable derivatives" is meant any pharmaceutically acceptable salt, ester, or salt of such ester, of compounds of formula (I) or (II) or any other compound such as a prodrug which, upon administration to the recipient, is capable of providing (directly or indirectly) compounds of formula (I) or (II) or an active metabolite or residue thereof.

The present invention also provides pharmaceutical compositions which comprise a pharmaceutically effective amount of a compound of the invention, or pharmaceutically acceptable salts thereof, and preferably, a pharmaceutically acceptable carrier, diluent or adjuvant. The term "pharmaceutically effective amount" is the amount of compound required upon administration to a mammal in order to induce analgesia. Also, the term "opioid receptor agonizing amount" refers to the amount of compound administered to a mammal necessary to bind and/or activate opioid receptors in vivo.

Therapeutic methods of this invention comprise the step of treating patients in a pharmaceutically acceptable manner with those compounds or compositions. Such compositions may be in the form of tablets, capsules, caplets, powders, granules, lozenges, suppositories, reconstitutable powders, or liquid preparations, such as oral or sterile parenteral solutions or suspensions.

In order to obtain consistency of administration, it is preferred that a composition of the invention is in the form of a unit dose. The unit dose presentation forms for oral administration may be tablets and capsules and may contain conventional excipients. For example, binding agents, such as acacia, gelatin, sorbitol, or polyvinylpyrolidone; fillers, such as lactose, sugar, maize-starch, calcium phosphate, sorbitol or glycine; tabletting lubricants such as magnesium stearate; disintegrants, such as starch, polyvinylpyrrolidone, sodium starch glycollate or microcrystalline cellulose; or pharmaceutically acceptable wetting agents such as sodium lauryl sulphate.

The compounds may be administered orally in the form of tablets, capsules, or granules containing suitable excipients such as starch, lactose, white sugar and the like. The compounds may be administered orally in the form of solutions which may contain coloring and/or flavoring agents. The compounds may also be administered sublingually in the form of tracheas or lozenges in which each active ingredient is mixed with sugar or corn syrups, flavoring agents and dyes, and then dehydrated sufficiently to make the mixture suitable for pressing into solid form.

The solid oral compositions may be prepared by conventional methods of blending, filling, tableting, or the like. Repeated blending operations may be used to distribute the active agent throughout those compositions employing large quantities of fillers. Such operations are, of course, conventional in the art. The tablets may be coated according to methods well known in normal pharmaceutical practice, in particular with an enteric coating.

Liquid oral preparations may be in the form of emulsions, syrups, or elixirs, or may be presented as a dry product for reconstitution with water or other suitable vehicle before use. Such liquid preparations may or may not contain conventional additives. For example suspending agents, such as sorbitol, syrup, methyl cellulose, gelatin, hydroxyethylcellulose, carboxymethylcellulose, aluminum stearate gel, or hydrogenated edible fats; emulsifying agents, such as sorbitan monooleate or acaci; non-aqueous vehicles (which may include edible oils), such as almond oil, fractionated coconut oil, oily esters selected from the group consisting of glycerine, propylene glycol, ethylene glycol, and ethyl alcohol; preservatives, for instance methyl para-hydroxybenzoate, ethyl para-hydroxybenzoate, n-propyl parahydroxybenzoate, or n-butyl parahydroxybenzoate of sorbic acid; and, if desired, conventional flavoring or coloring agents.

The compounds may be injected parenterally; this being intramuscularly, intravenously, or subcutaneously. For parenteral administration, the compound may be used in the form of sterile solutions containing other solutes, for example, sufficient saline or glucose to make the solution isotonic. For parenteral administration, fluid unit dosage forms may be prepared by utilizing the compound and a sterile vehicle, and, depending on the concentration employed, may be either suspended or dissolved in the vehicle. Once in solution, the compound may be injected and filter sterilized before filling a suitable vial or ampoule and subsequently sealing the carrier or storage package. Adjuvants, such as a local anesthetic, a preservative or a buffering agent, may be dissolved in the vehicle prior to use. Stability of the pharmaceutical composition may be enhanced by freezing the composition after filling the vial and removing the water under vacuum, (e.g., freeze drying the composition). Parenteral suspensions may be prepared in substantially the same manner, except that the compound should be suspended in the vehicle rather than being dissolved, and, further, sterilization is not achievable by filtration. The compound may be sterilized, however, by exposing it to ethylene oxide before suspending it in the sterile vehicle. A surfactant or wetting solution may be advantageously included in the composition to facilitate uniform distribution of the compound.

The pharmaceutical compositions of this invention comprise a pharmaceutically effective amount of a compound of this invention and a pharmaceutically acceptable carrier. Typically, they contain from about 0.01% to about 99% by weight, preferably from about 10% to about 60% by weight, of a compound of this invention, depending on which method of administration is employed.

The compounds of the present invention can be administered in combination with one or more further therapeutic agents. Preferably, the one or more further therapeutic agent is selected from the group consisting of nonsteroidal anti-inflammatory drugs (NSAIDs), acetaminophen, narcotics, antidepressants, anticonvulsants, corticosteroid, tramadol, sumatriptan, and capsaicin.

Without limitations, NSAIDs include aspirin (Anacin, Bayer, Bufferin), ibuprofen (Motrin, Advil, Nuprin), naproxen sodium (Aleve) and ketoprofen (Orudis KT)

Without limitations, narcotics include drugs derived from opium (opiates), such as morphine and codeine, and synthetic narcotics (opioids), such as oxycodone, methadone and meperidine (Demerol).

Without limitations, antidepressants include amitriptyline (Elavil), trazodone (Desyrel) and imipramine (Tofranil) may be used with other analgesics. These drugs are especially useful for neuropathic, head and cancer pain.

Without limitations, anticonvulsants include drugs developed for epilepsy, these drugs, such as phonation (Dilantin) and carbamazepine (Tegretol), can also help control chronic nerve pain.

Tramadol (Ultram) is a synthetic analgesic used primarily for chronic pain, but is also prescribed for acute pain.

Sumatriptan (Imitrex), may reduce pain from migraine headache by constricting blood vessels.

Capsaicin (Zostrix), a topical cream made from an extract of red peppers, can help relieve skin sensitivity resulting from shingles. Capsaicin can also be used to treat pain from arthritis, cluster headaches, diabetic neuropathy and pain after mastectomy.

In another aspect of the invention, compounds may be used to identify opioid receptors from non-opioid receptors. For such use, compounds of the invention are radiolabeled e.g. by incorporating 3H or 14C within its structure or by conjugation to 125I. Such radiolabeled forms can be used directly to identify the presence of opioid receptors and in particular p opioid receptors in a receptor population. This can be achieved by incubating membrane preparations with a radiolabeled compound of the invention. The presence and or amount of opioid receptors in the preparation is determined from the difference in membrane-bound radioactivity against a control preparation devoid of opioid receptors. Furthermore, radiolabeled forms of the present compounds can be exploited to screen for more potent opioid ligands, by determining the ability of the test ligand-to displace the radiolabeled compound of the present invention.

To further assist in understanding the present invention, the following non-limiting examples are provided. Certain abbreviations used throughout the examples can be found in the Aldrich Chemical Company and Bachem catalogues.

EXAMPLE 1

Synthesis of trans-7-Amino-8,8-dimethyl-6-methylsulfanyl-5,6,7,8-dihydro-naphthalen-2-ol, hydrochloride

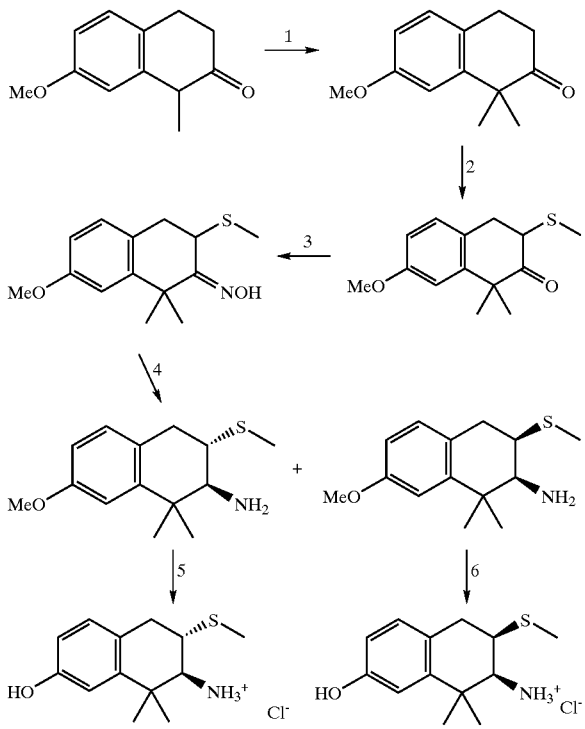

EXAMPLE 1

Synthesis of trans and cis-7-Amino-8,8-dimethyl-6-methylsulfanyl-5,6,7,8-dihydro-naphthalen-2-ol, hydrochloride Step 1: 7-Methoxy-1,1-dimethyl-3,4-dihydro-1H-naphthalen-2-one (A)

To a solution of 7-methoxy-1-methyl-3,4-dihydro-1H-naphthalen-2-one (1.95 g, 10.3 mmol) in THF (30 ml) was added NHMDS (11.3 mmol, 11.3 ml, 1M in THF) at 0° C. under nitrogen. The resulted solution was stirred at 0° C. for 1 hr. Iodomethane (7.29 g, 3.19 ml, 51.3 mmol) was added and stirred for an additional 3 hrs. 10% $KHSO_4$ aqueous solution was added to acidify the reaction mixture, diluted with brine, extracted with ethylacetate, washed with brine, dried over $MgSO_4$, filtered. The filtrate was evaporated under vacuo. The residue was purified by chromatography using ethylacetate:hexane (0.9:9.5) as eluant to give the desired product as white solid. (1.77 g, 85%). $^1$H NMR ($CDCl_3$) δ: 7.08(d, 1H, J=8.3 Hz), 6.88(d, 1H, J=2.7 Hz), 6.74(dd, 1H, J=2.7 and 8.3 Hz), 3.80(s, 3H), 3.03(t, 2H, J=6.6 Hz), 2.65(t, 2H, J=6.6 Hz), 1.42(s, 6H). $^{13}$C NMR ($CDCl_3$) δ: 213.7, 157.8, 143.9, 128.1, 126.5, 111.3, 110.4, 54.4, 46.9, 36.5, 26.8, 25.8.

Step 2: 7-Methoxy-1,1-dimethyl-3-methylsulfanyl-3,4-dihydro-1H-naphthalen-2-one(B)

To a solution of 7-methoxy-1,1-dimethyl-3,4-dihydro-1H-naphthalen-2-one (1.72 g, 8.40 mmol) in THF (20 ml) was added LHMDS (8.82 mmol, 8.82 ml, 1M in THF) at −78° C. under nitrogen, and then the temperature was raised to 0° C. and stirred for 1 hr. The solution was cooled to −78° C. and methylmethanathiosulfonate (0.87 ml, 1.06 g, 8.40 mmol) was added and stirring was continued for 4 hr at 0° C., then room temperature for 1 hr. The reaction mixture was quenched with 1N HCl (2 ml). Then, it was partitioned between ethylacetate and brine, washed with sat. $NaHCO_3$ aqueous solution, brine, then dried over $MgSO_4$, filtered, and evaporated under vacuo. The crude product was purified by flash column chromatography using ethylacetate:hexane (0.5:9.5 V/V) as eluant to give the desired product as white solid (2.07 g, 89%). $^1$H NMR ($CDCl_3$) δ: 7.06(d, 1H, J=7.2 Hz), 6.89(d, 1H, J=2.5 Hz), 6.73(dd, 1H, J=7.2 and 2.5 Hz), 3.79(s, 3H), 3.43(m, 1H), 3.40(m, 1H), 3.05(m, 1H), 2.05(s, 3H), 1.61(s, 3H), 1.37(s, 3H). $^{13}$C NMR ($CDCl_3$) δ: 208.3, 159.2, 144.6, 129.4, 124.0, 111.8, 110.9, 55.1, 50.2, 46.5, 32.7, 29.6, 27.2, 14.7.

Step 3: 7-Methoxy-1,1-dimethyl-3-methylsulfanyl-3,4-dihydro-1H-naphthalen-2-one oxime (C)

To a solution of 7-methoxy-1,1-dimethyl-3-methylsulfanyl-3,4-dihydro-1H-naphthalen-2-one (0.265 g, 1.05 mmol) in pyridine (5 ml) was added hydroxyamine hydrochloride (1.09 g, 15.7 mmol). The mixture was stirred under nitrogen at 85° C. overnight. The solution was cooled to room temperature, poured into water, extracted with ethylacetate, washed with 10% $KHSO_4$ aqueous solution, brine, dried over $MgSO_4$, filtered. The filtrate was evaporated under vacuo. The crude product was purified by flash column chromatography using ethylacetate:Hexane (1:9) as eluant to give the desired product as white solid (0.177 g, 63%). $^1$H NMR ($CDCl_3$) δ: 8.80(br, 1H), 7.05(d, 1H, J=8.2 Hz), 6.93(d, 1H, J=2.5 Hz), 6.73(dd, 1H, J=8.2 and 2.5 Hz), 4.91(t, 1H, J=3.0 Hz), 3.81(s, 3H), 3.26(dd, 1H, J=15.6 and 5.0 Hz), 2.96(dd, 1H, J=15.6and 3.0 Hz), 2.15(s, 3H), 176(s, 3H), 1.48(s, 3H). $^{13}$C NMR ($CDCl_3$) δ: 164.5, 159.1, 145.0, 129.6, 129.4, 111.8, 111.0, 55.3, 39.8, 35.9, 32.9, 32.4, 30.8, 15.1.

Step 4: 7-Methoxy-1-dimethyl-3-methylsulfanyl-3,4-dihydro-1H-naphthalen-2-ylamine (mixture of cis and trans) (D)

To a solution of 7-methoxy-1,1-dimethyl-3-methylsulfanyl-3,4-dihydro-1H-naphthalen-2-one oxime (1.13 g, 4.21 mmol) and sodium borohydride (0.669 g, 17.69 mmol) in 1,2-dimethoxyethane (20 ml) was added titanium tetrachloride (8.84 ml, 8.84 mmol, 1M in dichloromethane) dropwise under nitrogen at 0° C. The mixture was refluxed for 3 hrs. Then it was cooled to room temperature. Water (5 ml) was added slowly, then Sat.NaHCO$_3$ to aqueous solution (100 ml) was added. It was extracted with ethylacetate (3×100 ml). The combined extractions were dried over MgSO$_4$, filtered. The filtrate was evaporated under vacuo. The residue was purified by flash chromatography using ethylacetate as eluant to give the desired product as a mixture of cis:trans (1:1) (0.655 g, 61%). The mixture was further separated by reverse HPLC with gradient condition (10 to 50% acetonitrile/water (0.1% TFA). The aqueous solution was basified with sat. NaHCO$_3$ aqueous solution, extracted with ethylacetate, dried over MgSO$_4$, filtered. The filtrate was evaporated under vacuo to give cis isomer (C-18 HPLC fast isomer, 0.230 g, 21.5%) and trans isomer (C-18 HPLC slow isomer, 0.147 g, 14%) as white solid. $^1$H NMR (CDCl$_3$) δ: cis isomer, 6.97(d, 1H, J=8.2 Hz), 6.84(d, 1H, J=2.8 Hz), 6.69(dd, 1H, J=2.8 and 8.2 Hz), 3.77(s, 3H), 3.67(oct, 1H, J=14.57, 6.31, and 2.20 Hz), 2.75–2.97(m, 3H), 2.15(s, 3H), 1.49(s, br, 2H), 147(s, 3H), 1.25(s, 3H). $^{13}$C NMR (CDCl$_3$) δ: cis isomer, 158.40, 144.03, 129.57, 125.49, 112.37, 111.46, 57.22, 55.11, 44.41, 39.30, 32.53, 30.13, 26.48, 13.65. $^1$H NMR (CDCl$_3$) δ: trans isomer, 6.95(d, 1H, J=8.5 Hz), 6.87(d, 1H, J=2.4 Hz), 6.70(dd, 1H, J=8.5 and 2.4 Hz), 3.79(s, 3H), 3.18(m, 1H), 3.00–2.68(m, 3H), 2.15(s, 3H), 1.75(s, br, 2H), 1.46(s, 3H), 1.18(s, 3H). $^{13}$C NMR (CDCl$_3$) δ: trans isomer, 158.2, 146.4, 129.3, 126.1, 112.4, 111.6, 59.0, 55.2, 46.0, 40.2, 36.0, 27.9, 24.8, 12.1.

Step 5: (±)-Trans-7-Amino-8,8-dimethyl-6-methylsulfanyl-5,6,7,8-dihydro-naphthalen-2-ol, hydrochloride (compound #1)

To a solution of trans-7-methoxy-1,1-dimethyl-3-methylsulfanyl-3,4-dihydro-1H-naphthalen-2-ylamine (0.147 g, 0.585 mmol) in dichloromethane (10 ml) was added borontribromide (1.76 ml, 1.76 mmol, 1M in dichloromethane) dropwise at −78° C. under nitrogen. The mixture was slowly warmed to room temperature and stirred overnight. Sat. NaHCO$_3$ aqueous solution (5 ml) was added and stirred for 30 min. Then it was extracted with ethylacetate, dried over MgSO$_4$, filtered. The filtrate was evaporated under vacuo. The residue was dissolved in dichloromethane and HCl (1.8 ml, 1M in diethylether) was added. The solvent was evaporated. The residue was redissolved in dichloromethane, then it was added to hexane to precipitate the product. The precipitate was filtered off to give the desired product as white solid (0.13 g, 89%). $^1$H NMR (CD$_3$OD) δ: 6.92(d, 1H, J=8.2 Hz), 6.80(d, 1H, J=2.4 Hz), 6.63(dd, 1H, J=8.2 and 2.4 Hz), 3.37(d, 1H, J=11.2 Hz), 3.20–3.00(m, 3H), 2.20(s, 3H), 1.52(s, 3H), 1.2–9(s, 3H). $^{13}$C NMR (CD$_3$OD) δ: 157.0, 147.3, 130.4, 126.0, 114.7, 114.0, 60.3, 47.0, 40.9, 37.0, 28.5, 25.4, 11.8. LRMS, m/z, M+1, 238.0.

Step 6: (±)-Cis-7-Amino-8,8-dimethyl-6-methylsulfanyl-5,6,7,8-dihydro-naphthalen-2-ol, hydrochloride (compound #2)

To a solution of cis-7-methoxy-1,1-dimethyl-3-methylsulfanyl-3,4-dihydro-1H-naphthalen-2-ylamine (0.230 g, 0.905 mmol) in dichloromethane (10 ml) was added borontribromide (2.71 ml, 2.71 mmol, 1M in dichloromethane) dropwise at −78° C. under nitrogen. The mixture was slowly warmed to room temperature and stirred overnight. Sat. NaHCO$_3$ aqueous solution (5 ml) was added and stirred for 30 min. Then it was extracted with ethylacetate, dried over MgSO$_4$, filtered. The filtrate was evaporated under vacuo. The residue was dissolved in dichloromethane and HCl (1.8 ml, 1M in diethylether) was added. Solvent was evaporated. The residue was redisolved in dichloromethane. Then it was added to hexane to precipitate the product. The precipitate was filtered off to give the desired product as white solid (0.200 g, 80%). $^1$H NMR (CD$_3$OD) δ: 6.96(d, 1H, J=8.3 Hz), 6.81(d, 1H, J=2.4 Hz), 6.66(dd, 1H, J=2.4 and 8.3 Hz), 3.65(oct, 1H, J=2.2, 8.0, and 14.6 Hz), 3.47(d, 1H, J=2.2 Hz), 3.11(dd, 1H, J=2.2 and 8.0 Hz), 2.58(dd, 1H, J=8.0 and 14.6 Hz), 2.24(s, 3H), 1.54(s, 3H), 1.39(s, 3H). $^{13}$C NMR (CD$_3$OD) δ: 157.3, 144.9, 125.5, 114.7, 114.1, 57.9, 45.4, 39.9, 33.1, 31.2, 27.2, 13.5. LRMS, m/z, M+1, 238.1.

EXAMPLE 2

Synthesis of trans-7-Amino-8,8-diethyl-6-methylsulfanyl-5,6,7,8-dihydro-naphthalen-2-ol, hydrochloride (COMPOUND #3)

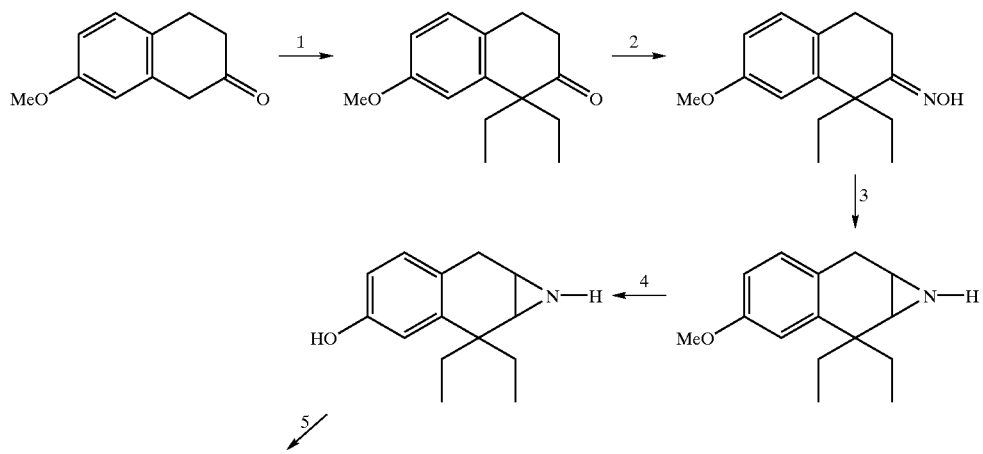

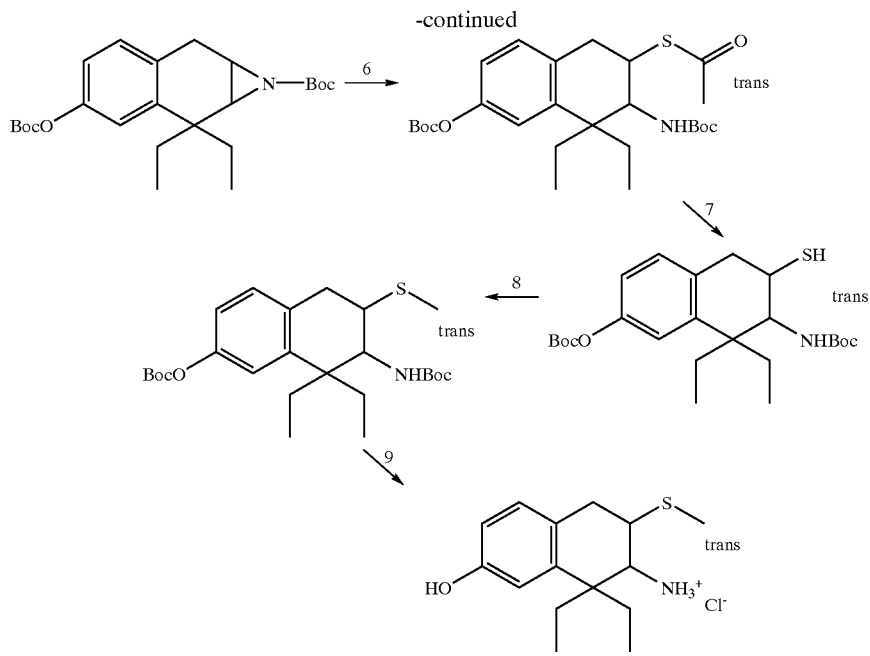

EXAMPLE 2

Synthesis of (±)-Trans-7-Amino-8,8-diethyl-6-methylsulfanyl-5,6,7,8-dihydro-naphthalen-2-ol, hydrochloride (compound #3)

Step 1: 1,1-Diethyl-7-methoxy-3,4-dihydro-1H-naphthalen-2-one (A)

To a solution of 7-methoxy-2-tetralone (4.26 g, 24.18 mmol) in DMF (100 mL) at 0° C. was 1 eq of sodium hydride (60% in oil) (1 g, 41.6 mmol). After 30 minutes, 1.25 eq of iodoethane was added (2.5 mL, 30.2 mmol), then after 30 min, the other equivalent of sodium hydride (1 g), after 30 min the iodoethane was added (2.5 mL, 30.2 mmol). The resulting purpule solution was stirred for 1 h at 0° C. then stirred for over night at r.t. The mixtutre was quenched with water, then diluted with $Et_2O$. The organic layer was then washed with $H_2O$, brine, dried over $MgSO_4$, filtered then evaporated. The residu was purified by a flash chromatography (5%AcOEt/Hex) (4.40 g, 78%). $^1H$ NMR ($CDCl_3$): 7.12 (1H, d, J=8.0 Hz, $H_5$), 6.78 (2H, m, $H_6$ and $H_8$), 3.84 (3H, s, $OCH_3$), 2.97 (2H, t, J=6.0 Hz, $PhCH_2$), 2.6 (2H, t, J=6.0 Hz, $CH_2CO$), 2.10 (2H, m, $CH_2$), 1.71 (2H, m, $CH_2$), 0.63 (6H, t, J=7.5 Hz, $CH_3$).

Step 2: 1,1-Diethyl-7-methoxy-3,4-dihydro-1H-naphthalen-2-one oxime (B)

1,1-diethyl-7-methoxy-3,4-dihydro-1H-naphthalen-2-one (4.40 g, 18.96 mmol) in dry pyridine (20 mL) with the hydroxylamine hydrochloride salt (10.54 g, 151.7 mmol) was heated to 80 ° C. for one day. The mixture was cooled down to r.t., then the pyridine was removed under vaccum. The green gum was dissolved with AcOEt, washed with $H_2O$, HCl 10%, $H_2O$, brine, dried over $MgSO_4$ and filtered through a small silica pad. The crude compound was used without any other purification (4.69 g, 100%). 1H NMR ($CDCl_3$): 7.94 (1H, s, OH), 7.06 (1H, d, J=8 Hz, $H_5$), 6.84 (1H, d, J=2.5 Hz, $H_8$), 6.73 (1H, dd, J=2.5 and 8 Hz, $H_6$), 3.83 (3H, s, $OCH_3$), 2.80–2.75 (4H, m, $PhCH_2CH_2$), 2.08 (2H, m, $CH_2$), 1.85 (2H, m, $CH_2$), 0.68 (6H, t, J=7.5 Hz, $CH_3$).

Step 3: 7,7-Diethyl-5-methoxy-1a,2,7,7a-tetrahydro-1H-1-aza-cyclopropa[b]naphthalene (C)

To a solution of the 1,1-diethyl-7-methoxy-3,4-dihydro-1H-naphthalen-2-one oxime (4.68 g, 18.96 mmol) in dry THF (100 mL) at 0° C. was added the diethylamine (4.9 mL, 47.4 mmol) and the LAH (95% powder) (2.16 g, 56.9 mmol). The mixture was stirred at 0° C. for 15 min then heated to reflux for 3 h. The gray solution was cooled down to 0° C., quenched with brine and diluted with AcOEt. The organic layer was decanted, washed with $H_2O$ (2×), brine, dried over $MgSO_4$, filtered then evaporated. The residu was purified by a flash chromatography (3% $MeOH/CH_2Cl_2$) (3.889 g, 89%). $^1H$ NMR ($CDCl_3$): 6.99 (1H, d, J=8 Hz, $H_5$), 6.76 (2H, m, $H_6$ and $H_8$), 3.13 (2H, m, CHCH), 2.40 (1H, broad, NH), 2.10–2.05 (2H, m), 1.84 (1H, m), 1.62 (4H, m, $CH_2$), 1.02 (3H, t, J=7.5 Hz, $CH_3$), 0.75 (3H, t, J=7.5 hz, $CH_3$).

Step 4: 7,7-Diethyl-1a2 7,7a-tetrahydro-1H-1-aza-cyclopropa[b]naphthalen-5-ol (D)

To a solution of 7,7-diethyl-5-methoxy-1a,2,7,7a-tetrahydro-1H-1-aza-cyclopropa[b]naphthalene (3.889 g, 16.81 mmol) in $CH_2Cl_2$ (170 mL) at −78° C. was added the $BBr_3$ (1M in $CH_2Cl_2$) (33.6 mL, 33.62 mmol). The mixture was kept at −78° C. for 30 min then to 0° C. for 1.5 h. The mixture was quenched by $NaHCO_3$, diluted with AcOEt. The organic layer was washed with $H_2O$, brine, dried over $MgSO_4$, filtered then evaporated. The residu was purified by a flash chromatography (3% MeOH/CH2C12) (2.917 g, 80%). $^1H$ NMR ($CDCl_3$): 6.93 (1H, d, J=8 Hz, $H_5$), 6.68 (1H, d, J=2.5 Hz, $H_8$), 6.64 (1H, dd, J=8 and 2.5 Hz, $H_6$), 3.12 (2H, m, CHCH), 2.42 (1H, broad, OH),2.14 91H, broad, NH), 2.04 (1H, m), 1.82 (1H, m), 1.65 (4H, m, $CH_2$), 1.02 (3H, t, J=7.5 Hz, $CH_3$), 0.75 (3H, t, J=7.5 hz, $CH_3$).

Step 5: 5-tert-Butoxycarbonyloxy-7,7-diethyl-1a,2,7,7a-tetrahydro-1-aza-cyclopropa[b]naphthalene-1-carboxylic acid tert-butyl ester (D)

To a solution of diethyl-1a,2,7,7a-tetrahydro-1H-1-aza-clopropa[b]naphthalen-5-ol (1.5 g, 6.90 mmol) in $CH_2Cl_2$ (30 mL) at r.t was added the (Boc)O (3.77 g, 17.26 mmol), the triethylamine (3.85 mL, 27.6 mmol) and DMAP (cat). The mixture was strirred at r.t for over night. The mixture was quenched by NH$_4$Cl, diluted with AcOEt. The organic layer was washed with H$_2$O, brine, dried over MgSO$_4$, filtered then evaporated. The residu was purified by a flash chromatography (5% to 25% AcOEt/Hex) (2.44 g, 84%). $^1$H NMR (CDCl$_3$): 7.05–6.95 (3H, m, Har), 3.29 (1H, d, J=17 Hz, PhC<u>H</u>H), 3.04 (1H, dd, J=2 Hz and 17 Hz, PhCH<u>H</u>), 2.94 (1H, m), 2.67 (1H, d, J=6.5 Hz), 2.05–1.95 (2H, m), 1.65–1.50 (11H, m), 1.43 (9H, s, t-butyl), 1.11 (3H, t, J=7.5 Hz, CH$_3$), 0.72 (3H, t, J=7.5 Hz, CH$_3$).

Step 6: Thioacetic acid S-(trans-3-tert-butoxycarbonylamino-6-tert-butoxycarbonyloxy-4,4-diethyl-1,2,3,4-tetrahydro-naphthalen-2-yl) ester (E)

5-tert-Butoxycarbonyloxy-7,7-diethyl-1a,2,7,7a-tetrahydro-1-aza-cyclopropa[b]naphthalene-1-carboxylic acid tert-butyl ester (218 mg, 0.52 mmol) and the thiolacetic acid (2 mL) was stirred at r.t for over night. The mixture was diluted with Et$_2$O (50 mL), washed with H$_2$O, NaHCO$_3$ (3×), H$_2$O, brine, dried over MgSO$_4$. The residu was purified by a flash chromatrgraphy (10% AcOEt/Hex) (234 mg, 91%). $^1$H NMR (CDCl$_3$): 7.05–6.95 (3H, m, Har), 4.80 (1H, d, J=10.5 Hz, NH), 4.15–4.00 (2H, m, CHCH), 3.17 (1H, dd J=5 Hz and 17 Hz, PhC<u>H</u>H), 2.97 (1H, dd, J=12 Hz and 17 Hz, PhCH<u>H</u>), 2.40 (3H, s, SCOCH$_3$), 1.86 (1H, m), 1.70 (2H, m), 1.60–1.55 (11H, m), 1.47 (9H, s, t-butyl), 0.89 (3H, t, J=7.5 Hz, CH$_3$), 0.71 (3H, t, J=7.5 Hz, CH$_3$).

Step 7: Carbonic acid 7-tert-butoxycarbonylamino-8,8-diethyl-trans-6-mercapto-5,6,7,8-tetrahydro-naphthalen-2-yl ester tert-butyl ester (F)

Thioacetic acid S-(trans-3-tert-butoxycarbonylamino-6-tert-butoxycarbonyloxy-4,4-diethyl-1,2,3,4-tetrahydro-naphthalen-2-yl) ester (234 mg, 0.47 mmol) in MeOH (5 mL) was added the sodium methoxide (54 μL, 0.95 mmol) and stirred at 0° C. for 30 min. The mixture was quenched with H$_2$O, diluted with Et$_2$O (50 mL), washed with H$_2$O, HCl (10%), H$_2$O, brine, dried over MgSO$_4$. The residu was used without any other purification (151 mg, 71%). $^1$H NMR (CDCl$_3$): 7.10–6.95 (3H, m, Har), 4.58 (1H, d, J=11.0 Hz, NH), 4.00 (1H, t, J=11 Hz, C<u>H</u>NH), 3.40–3.25 (2H, m), 2.98 (1H, m), 1.80–1.45 (22H, m), 0.80–0.70 (6H, m, CH$_3$).

Step 8: Carbonic acid 7-tert-butoxycarbonylamino-8,8-diethyl-trans-6-methylsulfanyl-5,6,7,8-tetrahydro-naphthalen-2-yl ester tert-butyl ester (G)

To a solution of carbonic acid 7-tert-butoxycarbonylamino-8,8-diethyl-trans-6-mercapto-5,6,7,8-tetrahydro-naphthalen-2-yl ester tert-butyl ester (28.2 mg, 0.062 mmol) in acetone (2 mL) was added the iodomethane (20 μL, 0.31 mmol) and the potassium carbonate (26 mg, 0.18 mmol), and stirred at reflux for 4 h. The mixture was quenched with H$_2$O, diluted with Et$_2$O (50 mL), washed with H$_2$O, brine, dried over MgSO$_4$. The residu was purified by a flash chromatography (10% AcOEt/Hex) (21.2 mg , 73%). $^1$H NMR (CDCl$_3$): 7.08 (1H, d, J=8.5 Hz, H$_5$), 7.00–6.95 (2H, m, H$_6$ and H$_8$), 4.56 (1H, d, J=11 Hz, NH), 4.09 (1H, t, J=11.0 Hz, C<u>H</u>NH), 3.25–3.00 (3H, m), 2.15 (3H , broad, SCH$_3$), 1.76 (4H, m, CH$_2$), 1.57 (9H, s, t-butyl), 1.50 (9H, s, t-butyl), 0.73 (6H, m, CH$_3$).

Step 9: (±)-Trans-1,1-diethyl-7-hydroxy-3-methylsulfanyl-1,2,3,4-tetrahydro-naphthalen-trans-2-yl-ammonium; chloride (compound #3)

To a solution of Carbonic acid 7-tert-butoxycarbonylamino-8,8-diethyl-trans-6-methylsulfanyl-5, 6,7,8-tetrahydro-naphthalen-2-yl ester tert-butyl ester (21.2 mg, 0.045 mmol), in CH$_2$Cl$_2$(2 mL) was added the TFA (0.2 mL). The solution was stirred at r.t for 3 h. The volatil was removed and co-evaporated with CH$_2$Cl$_2$. The final purety was verified by HPLC reversed phased (0% to 50% of CH$_3$CN+0.01% TFA in 25 min, λ=215 nM Rt=11.28 min, 97%) (14.8 mg, 86%). $^1$H NMR (CD$_3$OD): 6.99 (1H, d, J=8.5 Hz, H$_5$), 6.70–6.65 (2H, m, H$_6$ and H$_8$),4.46 (1H, d, J=11 Hz,), 3.30–3.25 (2H, m), 2.98 (1H, dd, J=5.5 Hz and 11 Hz, PhC<u>H</u>H), 2.22 (3H, s, SCH$_3$), 2.15 (1H, m, C<u>H</u>HCH$_3$), 1.77 (2H, m, C<u>H</u>$_2$CH$_3$), 1.64 (1H, m, CH<u>H</u>CH$_3$), 0.85 (3H, t, J=7.5 Hz, CH$_3$), 0.75 (3H, t, J=7.5 Hz, CH$_3$).

EXAMPLE 3

1,1-Dimethyl-7-hydroxy-3-phenylsulfanyl-1,2,3,4-tetrahydro-naphthalen-trans-2-yl-ammonium; chloride

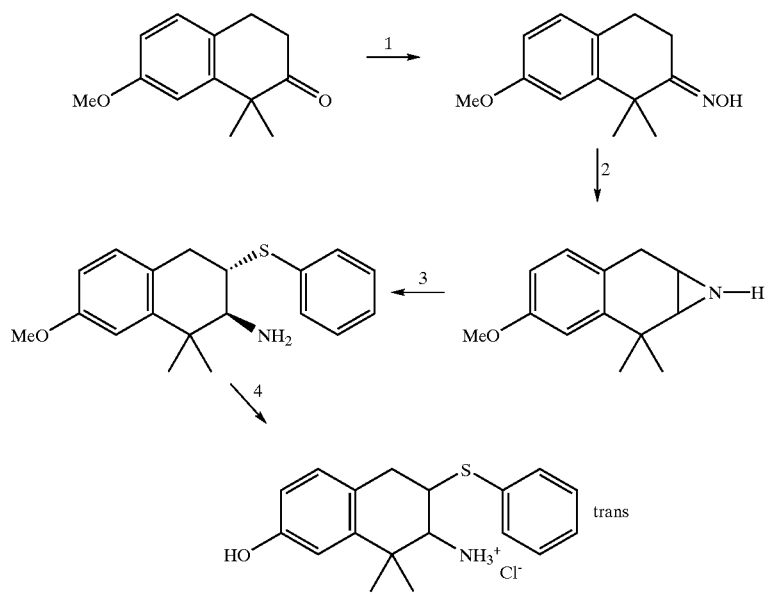

EXAMPLE 3

(±)-Trans-1,1-dimethyl-7-hydroxy-3-phenylsulfanyl-1,2,3,4-tetrahydro-naphthalen-trans-2-yl-ammonium; chloride (compound #4)

Step 1: 7-Methoxy-1,1-dimethyl-3,4-dihydro-1H-naphthalen-2-one oxime (A)

7-Methoxy-1,1-dimethyl-3,4-dihydro-1H-naphthalen-2-one (used as a crude from example 1, step1, 128.8 g, 0.63 mol) and hydroxylamine hydrochloride (350 g, 5.04 mol) in pyridine (360 ml) were heated up to 80° C. The reaction mixture was stirred for 15 h at 80–90° C. Pyridine was removed under reduced pressure. The residue was partitioned between ethylacetate (2.5 l) and water (1 l). Water layer was separated and washed with ethyl acetate (1 l). Ethyl acetate solution was washed with 10% aq. $KHSO_4$ (1 l), dried over $Na_2SO_4$. Ethyl acetate was removed under reduced pressure and the residue was crystallized from acetone to give 101.2 g of target compound. Mother liquid was concentrated to dryness and crystallized from acetone to give second crop (11.4 g). 112.6 g (82%) of the desired product was obtained. $^1$H NMR ($CDCl_3$), d 9.15 (s, 1H), 7.06 (d, 1H, J=7.4 Hz) 6.92 (1H, d, J=2.4 Hz), 6.75 (dd, 1H, J=7.4 and 2.4 Hz), 3.82 (s, 3H), 2.78–2.95 (m, 4H), 1.5 (s, 6H).

Step 2: 5-Methoxy-7,7-dimethylmethyl-1a,2,7,7a-tetrahydro-1H-1-aza-cyclopropa[b]naphthalene(B)

$LiAlH_4$ (1M in THF,1.431, 1.43 mol) was added dropwise to a solution of diethylamine (108 ml, 1.05 mol) and 7-Methoxy-1,1-dimethyl-3,4-dihydro-1H-naphthalen-2-one oxime (112.6 g, 0.51 mol) in THF (700 ml) at 0–8° C. The reaction mixture was brought to reflux and refluxed for 1 h. An excess of $LiAlH_4$ was quenched with water solids were filtered off and washed with 25% MeOH in acetone followed by 5% aq ammonia in MeOH. The solution was concentrated to dryness and the crude was purified by flash chromatography using ethylacetate/methanol (1 to 4%) with 0.2% of ammonia hydroxide. Fraction containing desired product were concentrated to dryness and the residue was crystallized from hexane to give 58 g (56%) of the target compound.

The mother liquid was purified by flash chromatography using hexane/ethyl acetate (1/1) followed by ethyl acetate to give 10 g (10%) of the target compound. $^1$H NMR ($CDCl_3$), d 6.98(d, 1H, J=7.8 Hz) 6.851H, d, J=2.4 Hz), 6.70(dd, 1H, J=7.8 and 2.4 Hz), 3.15 (br s, 2H), 2.51(br s, 1H), 2.15 (br s, 1H), 1.75 (s, 3H), 1.22 (s, 3H).

Step 3: 7-Methoxy-1,1-dimethyl-3-phenylsulfanyl-1,2,3,4-tetrahydro-naphthalen-trans-2-yl-amine(C)

4-Methoxy-2,2-dimethyl-1a,2,7,7a-tetrahydro-1H-1-aza-cyclopropa(b)naphthalene (0.352 g, 1.73 mmoles) was dissolved in 2 ml of ethyl alcohol. To the stirred solution, triethylamine (0.88 ml, 6.3 mmoles) and thiophenol (0.53 ml, 5.16 mmoles) were added subsequently. The reaction mixture was stirred for 24 hours at room temperature until TLC shows complete reaction. The solvent was removed by vacuum distillation. Resulting dark yellow oil, was dissolved in minimum quantity of dichloromethane and applied on Mega-Bond Elut cartridge. The desired product was isolated by elution with ethyl acetate and hexane mixture (1:3), (0.373 g, 65%). $^1$H NMR ($CDCl_3$) d: 7.51(d, 2H), 7.30(m, 3H), 6.89(m, 2H), 6.68(m, 1H), 3.79(s, 3H), 3.44(m, 1H), 3.11(dd, 1H), 2.88(dd, 2H), 1.66(br, 2H), 1.48(s, 3H), 1.20(s. 3H); ppm Step 4 1,1-Dimethyl-7-hydroxy-3-phenylsulfanyl-1,2,3,4-tetrahydro-naphthalen-trans-2-yl-ammonium; chloride (D)

Trans-7-Methoxy-1,1-dimethyl-3-phenylsulfanyl-1,2,3,4-tetrahydro-naphthalen-yl-amine (0.373 g, 1.19 mmoles) was dissolved at 0° C. in dichloromethane (30 ml). Solution of boron tribromide in dichloromethane (3.57 ml of 1M soln.) was slowly added. It was stirred for and allowed to reach room temperature within 2 hours. Stirring was continued for overnight. Saturated sodium bicarbonate was added to quench reaction. The product was extracted using dichloromethane (4×30 ml). Crude mixture was purified on Mega Bond Elut cartridge eluting with ethyl acetate. Fractions containing pure product were combined, evaporated and evacuated under high vacuum. The resulting solid was dissolved in warm methanol (10 ml) place in an ice bath and treated with 1.2 ml of 1M HCl in $Et_2O$. It was stirred for 25 min, evaporated to dryness, redissolved in 30 ml of water and freeze dried to give 0.1927 g (48%)of white solid. $^1$H NMR ($CD_3OD$) d: 7.62(d, 2H, J=6.46 Hz), 7.41(d, 3H, J=7.3 Hz), 7.79(dd, 2H, J=2 Hz, J=7 Hz), 6.59(dd, 1H, J=2 Hz, J=7 Hz), 3.54(m, 1H), 3.35(d, 1H), 3.11(dd, 1H, J=4.8 Hz, J=16 Hz), 2.84(dd, 1H, J=16 Hz, J=12 Hz, 1.52(s, 3H), 1.32(s, 3H); ppm.

EXAMPLE 4

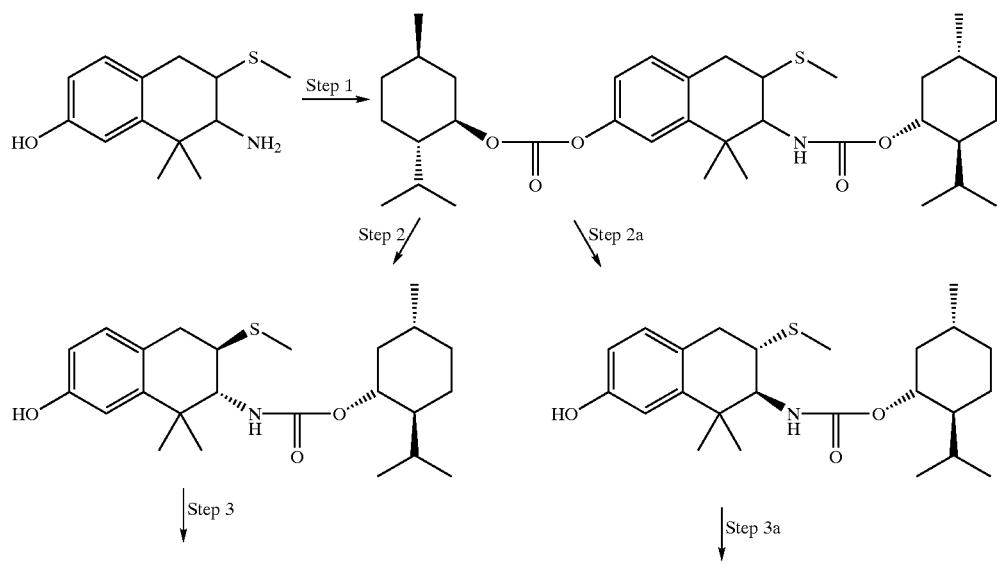

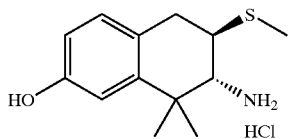 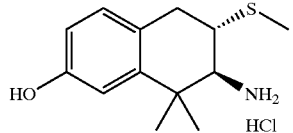

Step 1: (−)-Trans-[Carbonic acid 2-(S)-isopropyl-5-(R)-methyl-cyclohex-(R)-yl ester 7-(R)-(2-(S)-isopropyl-5-(R)-methyl-cyclohex-(R)-yloxycarbonyl-(R)-amino)-8,8-dimethyl-6-methylsulfanyl-5,6,7,8-tetrahydronaphthalen-2-yl ester]

Trans-7-Amino-8,8-dimethyl-6-methylsulfanyl-5,6,7,8-tetrahydro-naphthalen-2-ol (0.150 g, 0.6 mmoles), was dissolved in 30 ml of dichloromethane at 0° C. To a stirred solution, pyridine (0.240 ml, 3 mmoles), and (L)-(−)-menthyl chloroformate (0.320 ml, 1.5 mmoles) were added. The mixture was allowed to reach room temperature and it was further stirred for 2 hours. Aqueous sodium bicarbonate was added and stirred for 20 minutes. Organic phase was separated and aqueous layer was extracted with three portions of dichloromethane. Organic extracts were dried over anhydrous sodium sulfate, filtered and evaporated. Remaining oil was applied on preparative TLC plate and eluted three times with mixture of ethylacetate and hexane, 1:20. Less polar fraction contains (+) diastereomer (0.12 g), more polar fraction contains (−) diastereomer (0.09 g). $^1$H NMR (400 MHz) (CDCl$_3$; d; ppm): 7.12(m, 1H), 7.05(m, 1H), 6.98(m, 1H), 4.6(m, 3H), 3.9(t, 1H, J=6 Hz), 3.25(m, 1H), 3.15(m, 1H), 3.0(m, 1H), 2.2–2.0(m, 5H), 1.7(m, 4H), 1.5(m, 3H), 1.4(, m, 3H), 1.2(m, 3H), 1.1(m, 4H), 0.8–0.95 (m, 21H).

Step 2: (−)-Trans-7-Hydroxy-1,1-dimethyl-3-methylsulfanyl-1,2,3,4-tetrahydro-naphthalen-2-yl)-carbamic acid 2-isopropyl-5-methylcyclohexyl ester (−)-Trans-[Carbonic acid 2-(S)-isopropyl-5-(R)-methyl-cyclohex-(R)-yl ester 7-(R)-(2-(S)-isopropyl-5-(R)-methyl-cyclohex-(R)-yloxycarbonyl-(R)-amino)-8,8-dimethyl-6-methylsulfanyl-5,6,7,8-tetrahydronaphthalen-2-yl ester], (0.09 g, 0.2 mmoles), was dissolved in 2 ml of methyl alcohol containing potassium carbonate (0.01 g ). It was stirred for 5 hours at room temperature. Methyl alcohol was evaporated and the residue was applied on silicagel column. The product was eluted using ethylacetate:hexane mixture 1:5, (0.021 g). $^1$H NMR (400 MHz) (CD$_3$OD; d; ppm): 6.7(d, 0.8H, J=10 Hz), 6.65(d, 1H, J=8 Hz), 6.5(d, 1H, J=2 Hz), 6.3(dd, 1H, J=2 Hz, J=8 Hz), 4.6(s, 3H), 4.3(m, 1H), 3.45(m, 1H), 3.1(m, 3H), 2.9(dd, 1H, J=6 Hz, J=12 Hz), 2.8(m, 1H), 2.7(m, 1H), 1.9(s, 2H), 1.85(m, 1H), 1.5(d, 1H, J=10 Hz), 1.3–1.2(m, 2H), 1.1(s, 2H), 0.95(s, 2H), 0.7(d, 3H, J=5 Hz), 0.6(d, 3H, J=5 Hz).

Step 3: (−)-Trans-7-amino-8,8-dimethyl-6-methylsulfanyl-5,6,7,8-tetrahydro-naphthalen-2-ol hydrochloride (−)-Trans-7-Hydroxy-1,1-dimethyl-3-methylsulfanyl-1,2,3,4-tetrahydro-naphthalen-2-yl)-carbamic acid 2-isopropyl-5-methylcyclohexyl ester (0.021 g), was dissolved in a mixture of acetic acid solution of HBr (36%) 0.5 ml, and formic acid (1 m). The flask was sealed and heated at 58–60° C. for 4 hours. The liquids were evaporated to dryness under vacuum and the residue was alkalized with aqueous ammonia. Alkaline solution was extracted with dichloromethane. Organic extracts were dried over sodium sulfate, foltered and evaporated. The residue was dissolved in MeOH (0.5 ml) and 1M solution of HCl in ethyl ether (0.2 ml) was added. It was stirred for 10 min., evaporated, dissolved in water (5 ml) and freeze dried. Yield: 0.0125 g of white solid; a$_D$=−65° (c=0.04, MeOH).

Compound #32 Trans-(−)-7-amino-8,8-dimethyl-methylsulfanyl-5,6,7,8-tetrahydro-naphthalen-2-ol hydrochloride

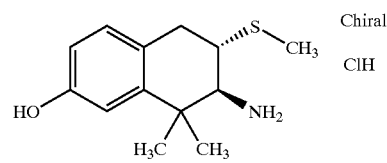

$^1$H NMR (CD$_3$OD; d; ppm): 6.92(d, 1H, J=10 Hz), 6.78(d, 1H, J=3 Hz), 6.63(dd, 1H, J=10 Hz, J=3 Hz), 3.31(1H), 3.10(m, 3H), 2.2(s, 3H), 1.5(s, 3H). 1.3(s, 3H).

Compound #33 Trans-(+)-7-amino-8,8-dimethyl-6-methylsulfanyl-5,6,7,8-tetrahydro-naphthalen-2-ol hydrochloride

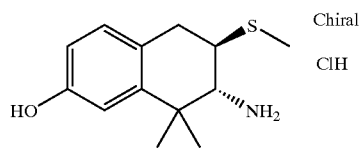

$^1$H NMR (CD$_3$OD; d; ppm): 6.92(d, 1H, J=10 Hz), 6.78(d, 1H, J=3 Hz), 6.63(dd, 1H, J=10 Hz, J=3 Hz), 3.31(1H), 3.10(m, 3H), 2.2(s, 3H), 1.5(s, 3H). 1.3(s, 3H).

In a similar manner as described in examples 1 to 4, the following compounds were also obtained:

Compound #5 (±)-Trans-7-hydroxy-1,1-dimethyl-3-(2-pyridylsulfanyl)-1,2,3,4-tetrahydronaphthalen-2-yl ammonium trifluoroacetate

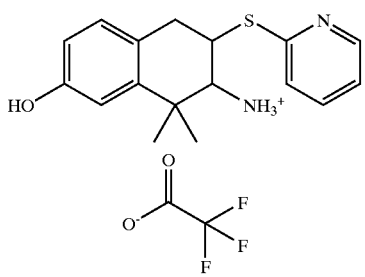

$^1$H NMR (CD$_3$OD), d 8.49 (d, 1H, J=5 Hz), 7.77–7.73(m, 1H), 7.49 (1H, d, J=8.1 Hz), 7.27–7.24(m, 1H), 6.92 (d, 1H,J=8.4 Hz), 6.84 (1H, d, J=2.5 Hz), 6.64 (dd, 1H, J=8.4 and 2.5 Hz), 4.23–4.15 (m, 1H), 3.60 (d, 1H, J=11.2 Hz), 3.28 (dd, 1H, J=18 Hz and J=5.3 Hz), 3.05 (dd, 1H, J=18 Hz, J=5.2 Hz), 1.55 (s, 3H), 1.43 (s, 3H)

Compound #6 (±)-Trans-7-hydroxy-1,1-dimethyl-3-(pyrimidyl-2-sulfanyl)-1,2,3,4-tetrahydronaphthalen-2-yl ammonium chloride

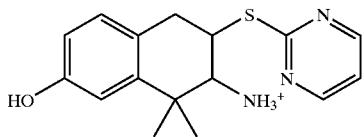

¹H NMR (CD₃OD), d 8.28 (s, 1H), 8.27 (s, 1H), 6.87 (d, 1H, J=8.3 Hz), 6.77 (d, 1H, J=2.4 Hz), 6.62–6.56. (m, 2H), 4.31 (d, 1H, J=11.6 Hz), 3.40–3.47 (m, 1H), 3.60 (d, 1H, J=11.2 Hz), 3.28 (dd, 1H, J=16.2 Hz and J=5.3 Hz), 2.93 (dd, 1H, J=16.2 Hz, J=5.2 Hz), 1.30 (s, 3H), 1.23 (s, 3H)

Compound #7 (±)-Trans-7-amino-6-(3-amino-phenylsulfanyl)8,8-dimethyl-5,6,7,8-tetrahydro-naphthalen-2-ol dihydrochloride

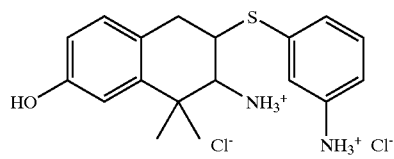

¹HNMR 7.06 (dd, 1H, J=7.9 Hz, J=7.8 Hz), 6.9 (dd, 1H, J=1.9 Hz, J=1.8 Hz), 6.82 (d, 1H, J=7.8 Hz), 6.77 (d, J=6.8 Hz), 6.76 (s, 2H), 6.62–6.65 (m, 1H), 6.53 (dd, 1H, J=2.5, J=8.3 Hz), 3.86–3.3.94(m, 1H), 3.06 (dd, 1H J=5.3 Hz, J=16.3 Hz), 2.82 (s, 1H), 2.72(s, 1H), 1.41 (s, 3H), 1.18 (s, 3H)

Compound #8 (±)-Trans-7-amino-6-(4-methylthio-phenylsulfanyl)-8,8-dimethyl-5,6,7,8-tetrahydro-naphthalen-2-ol hydrochloride

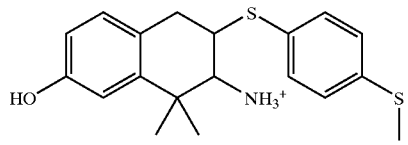

¹HNMR (CD₃OD), d 7.46 (dd, 2H, J=1.8 Hz, J=8.4 Hz), 7.24 (dd, 2H, J=1.8 Hz, J=8.4 Hz), 6.74–6.76 (m, 2H), 6.52 (dd, 1H, J=2.4 Hz, J=8.3 Hz). 3.29–3.36 (m, 1H), 3.00 (dd, 1H, J=5.3 Hz, J=16.2 Hz), 2.18–2.28 (m, 2H), 2.47 (s, 3H), 1.40 (s, 3H), 1.17 (s, 3H).

Compound #9 (±)-Trans-3-benzenesulfonylmethylsulfanyl-1,1-diethyl-7-hydroxy-1,2,3,4-tetrahydronaphthalen-2-yl-ammonium; chloride

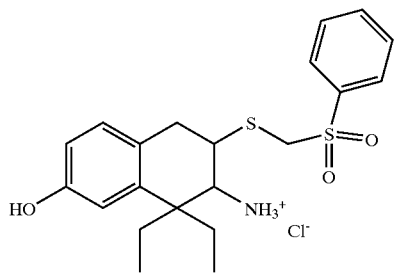

¹H NMR (MeOD): 8.02 (2H, d, J=8.0 Hz), 7.80 (1H, m), 7.70 (2H, t, J=8.0 Hz), 6.96 (1H, d, J=8.0 Hz), 6.70 (2H, m), 4.58 (2H, s), 3.72 (1H, m), 3.62 (1H, d, J=11.5 Hz), 2.93 (1H, dd, J=11.5 Hz and 16 Hz), 2.13 (1H, m), 1.85–1.65 (3H, m), 0.86 (3H, t, J=7.5 Hz), 0.73 (3H, t, J=7.5 Hz, m).

Compound #10 (±)-Trans-3-carbamoylmethylsulfanyl-1,1-diethyl-7-hydroxy-1,2,3,4-tetrahydro-naphthalen-2-yl-ammonium; trifluoro-acetate

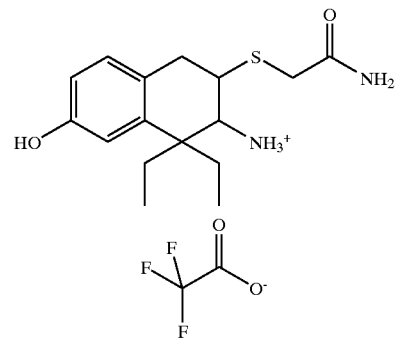

¹H NMR (DMSO): 9.23 (1H, s), 8.47 (3H, broad), 7.70–7.60 (2H, broad), 6.91 (1H, d, J=8.5 Hz), 6.61 (1H, s), 3.58 (2H, s), 3.11 (1H, m), 2.94 (1H, m), 1.93 (1H, m), 1.82 (1H, m), 1.65 (1H), 1.54 (1H, m), 0.71 (3H, t, J=7.5 Hz), 0.57 (3H, t, J=7.5 Hz).

Compound #11 (±)Trans-3-(diethoxy-phosphorylmethylsulfanyl)-1,1-diethyl-7-hydroxy-1,2,3,4-tetrahydro-naphthalen-2-yl-ammonium; chloride

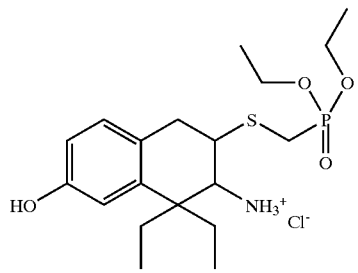

¹H NMR (DMSO): 9.23 (1H, s), 8.22 (3H, broad), 6.92 (1H, d, J=8.5 Hz), 6.61 (2H, m), 4.12 (4H, m), 3.20–3.15 (2H, m), 2.97 (1H, m), 1.95 (1H, m), 1.83 (1H, m), 1.65 (1H, m), 1.51 (1H, m,) 1.27 (6H, m), 0.71 (3H, t, J=7.5 Hz), 0.60 (3H, t, J=7.5 Hz).

Compound #12 (±)-Trans-1,1-diethyl-7-hydroxy-3-(2-hydroxy-ethylsulfanyl)-1,2,3,4-tetrahydro-naphthalen-2-yl-ammonium; chloride

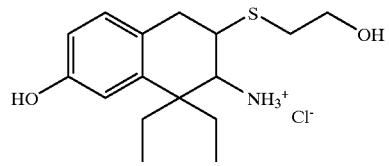

¹H NMR (MeOD): 6.97 (1H, d, J=8.0 Hz), 6.70–6.65 (2H, m), 3.82 (2H, m), 3.50–3.40 (2H, mm), 3.00–2.85 (2H, m), 2.12 (1H, m), 1.80–1.60 (3 h, m), 0.83 (3H, t, J=7.5 Hz), 0.73 (3H, t, J=7.5 Hz).

Compound #13 (±)-Trans-3-(5-amino-2H-[1,2,4]triazol-3-ylsulfanyl)-1,1-diethyl-7-hydroxy-1,2,3,4-tetrahydro-naphthalen-2-yl-ammonium; trifluoro-acetate

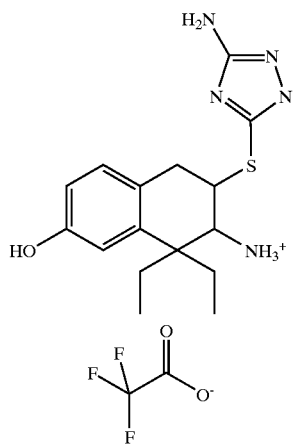

$^1$H NMR (MeOD): 6.97 (1H, d, J=8.5 Hz), 6.70–6.65 (2H, m), 3.90 (1H, qd, J=5.5 Hz and 12 Hz), 3.76 (1H, d, J=12 Hz), 3.29 (1H, dd, J=5.5 Hz and 16.5 Hz), 2.11 (1H, m), 1.85–1.65 (3H, m), 0.88 (3H, t, J=7.5 Hz), 0.70 (3H, t, J=7.5 Hz).

Compound #14 (±)-Trans-3-(2-Ammonium-ethylsulfanyl)-7-hydroxy-1,1-dimethyl-1,2,3,4-tetrahydro-naphthalen-2-yl-ammonium dichloride

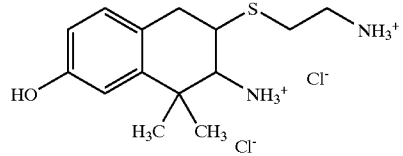

(400 MHz, CD$_3$OD) δ: 6.8(3H, m), 3.8–2.5(8H, m), 1.5 (3H, s), 1.32(3H, s).

Compound #15 (±)-Trans-3-(5-Amino-2H-[1,2,4]triazol-3-ylsulfanyl)-1,1-dimethyl-7-hydroxy-1,2,3,4-tetrahydro-naphthalen-2-yl-ammonium; chloride

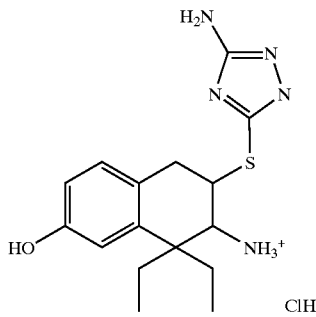

(400 MHz, DMSO-D$_6$) δ: 9.3(3H, bs), 8.3(3H, bs), 6.75 (3H, m), 3.9–3.0(4H, m), 1.45(3H, s), 1.15(3H,s).

Compound #16 (±)-Trans-1,1-dimethyl-7-hydroxy-3-propylsulfanyl-1,2,3,4-tetrahydro-naphthalen-2-yl-ammonium; trifluoro-acetate

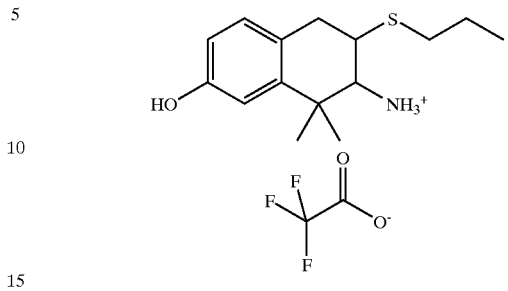

$^1$H NMR (DMSO): 9.22 (1H, s), 8.04 (3H, bs), 6.87 (1H, d, J=8.5 Hz), 6.74 (1H, d, J=2.0 Hz), 6.74 (1H, dd, J=2.0 Hz and 8.5 Hz), 3.28 (1H, m), 3.15–3.05 (2H, m), 2.91 (1H, m), 2.75–2.60 (2H, m), 1.60 (2H, m), 1.44 (3H, s), 1.19 (3H, s), 0.98 (3H, t, J=7.5 Hz).

MS: 266 (MH+)

Compound #17 (±)-Trans-1,1-dimethyl-7-hydroxy-3-isopropylsulfanyl-1,2,3,4-tetrahydro-naphthalen-2-yl-ammonium; chloride

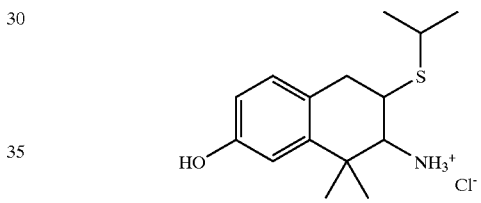

$^1$H NMR (DMSO): 9.23 (1H, s), 8.14 (3H, bs), 6.87 (1H, d, J=8.5 Hz), 6.75 (1H, d, J=2.0 Hz), 6.59 (1H, dd, J=2.0 Hz and 8.5 Hz), 3.29 (1H, m), 3.25–3.10 (3H, m), 2.84 (1H, td, J=10.5 Hz and 6.5 Hz), 1.43 (3H, s), 1.30 (3H, d, J=6.5 hz), 1.27 (3H, d, J=6.5 Hz), 1.22 (3H, s).

MS: 266 (MH+)

Compound #18 (±)-Trans-1,1-dimethyl-7-hydroxy-3-(2-hydroxy-ethylsulfanyl)-1,2,3,4-tetrahydro-naphthalen-2-yl-ammonium; chloride

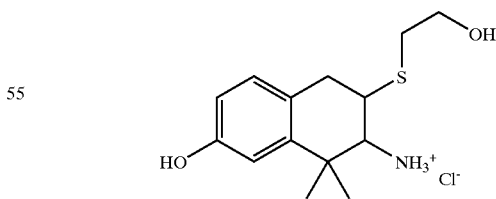

$^1$H NMR (DMSO): 9.23 (1H, s), 8.14 (3H, bs), 6.87 (1H, d, J=8.5 Hz), 6.74 (1H, d, J=2.0 Hz), 6.58 (1H, dd, J=2.0 Hz and 8.5 Hz), 5.32 (1H, broad), 3.70–3.60 (2H, m), 3.20–3.05 (2H, m), 2.95–2.75 (3H, m), 1.44 (3H, s), 1.19 (3H, s).

MS: 268 (MH+)

Compound #19 (±)-Trans-3-arbamoylmethylsulfanyl-1,1-dimethyl-7-hydroxy-1,2,3,4-tetrahydro-naphthalen-2-yl-ammonium; trifluoro-acetate

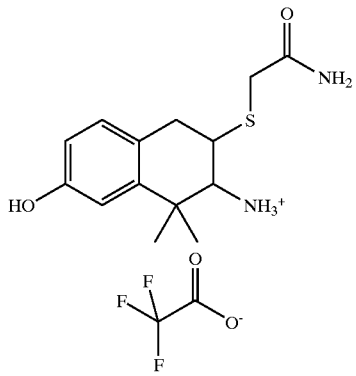

¹H NMR (DMSO): 9.23 (1H, s), 8.48 (3H, bs), 7.98 (1H, s), 7.59 (1H, s), 6.86 (1H, d, J=8.0 Hz), 6.74 (1H, s), 6.58 (1H, dd, J=2.0 Hz and 8.0 Hz), 3.55 (1H, d, J=16.0 Hz), 3.50–3.15 (3H, m), 2.99 (2H, d, J=8.0 Hz), 1.42 (3H, s), 1.17 (3H, s).

Compound #20 (±)-Trans-7-dimethylamino-8,8-dimethyl-6-methylsulfanyl-5,6,7,8-tetrahydro-naphthalen-2-ol

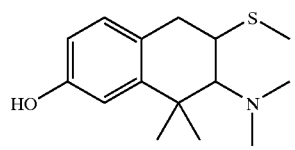

¹H NMR (400 MHz) (CDCl₃; d; ppm): 6.90 (1H, d), 6.78 (1H, d), 6.59 (1H, dd), 3.21 (1H, dd), 3.08 (1H, m), 2.93 (1H, dd), 2.64 (1H, d), 2.28 (6H, s) 2.21 (3H, s), 1.31 (3H, s), 1.30 (3H, s).

Compound #21 (±)-Trans-8,8-dimethyl-7-methylamino-6-methylsulfanyl-5,6,7,8-tetrahydro-naphthalen-2-ol

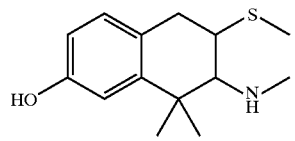

¹H NMR (400 MHz) (CDCl₃; d; ppm): 6.90 (1H, d), 6.80 (1H, d), 6.61 (1H, dd), 3.05 (1H, m), 2.95 (1H, m), 2.67 (3H, s), 2.36 (1H, d), 2.19 (3H, s), 1.43 (3H, s, CH₃), 1.20 (3H, s, CH₃).

Compound #22 (±)-Trans-7-Amino-8,8-diethyl-6-phenylsulfanyl-5,6,7,8-tetrahydro-naphthalen-2-ol

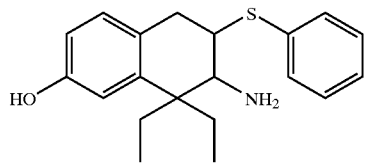

¹H NMR (400 MHz) (CDCl₃; d; ppm): 7.51 (1H, d), 7.27–7.34 (4H, m), 6.85 (1H, d), 6.66 (1H, d), 6.60 (1H, dd), 3.62 (1H, m), 3.12 (1H, dd), 2.83(1H, dd), 2.75–3.12 (2H, bs, NH₂), 1.84 (2H, m), 1.79 (1H, m), 1.67 (1H, m), 0.75 (3H, t, J=7.5 Hz, CH₃), 0.64 (3H, t, J=7.2 Hz, CH₃).

Compound #23 (±)-Trans-8,8-dimethyl-trans-6-phenylsulfanyl-7-propylamino-5,6,7,8-tetrahydro-naphthalen-2-ol

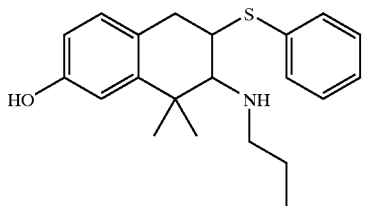

¹H NMR (400 MHz) (CDCl₃; d; ppm): 7.50 (2H, m), 7.32 (2H, m), 7.27 (1H, m), 6.81 (2H, m), 6.59 (1H, m), 3.77 (1H, m), 3.11 (1H, m), 2.89–3.02 (2H, m),2.47–2.76 (2H, m), 1.46 (2H, bs), 1.44 (3H, s), 1.27 (3H, s), 0.94 (3H, t, J=7.2 Hz).

Compound #24 (±)-Trans-7-Amino-6-(2-amino-phenylsulfanyl)-8,8-diethyl-5,6,7,8-tetrahydro-naphthalen-2-ol

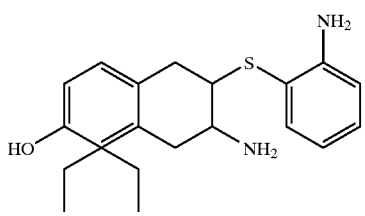

¹H NMR (400 MHz) (CDCl₃; d; ppm): 7.44 (1H, m), 7.15 (1H, m), 6.84 (1H, m), 6.74 (1H, m), 6.70 (1H, m), 6.64 (1H, d), 6.57 (1H, m), 3.46 (1H, m), 3.07 (1H, d), 3.02 (1H, dd), 2.82 (1H, dd), 1.81 (2H, m), 1.73 (1H, m), 1.59 (1H, m), 0.71 (3H, t, J=7.5 Hz), 0.65 (3H, t, J=7.3 Hz).

Compound #25 (±)-Trans-7-hydroxy-1,1-dimethyl-trans-3-(2,2,2-trifluoro-ethylsulfanyl)-1,2,3,4-tetrahydro-naphthalen-2-yl-ammonium chloride

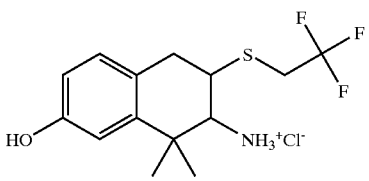

¹H NMR (400 MHz) (CD₃OD; d; ppm): 6.93 (1H, d), 6.80 (1H, d), 6.64 (1H, dd), 3.57 (2H, m), 3.40 (1H, d), 3.25–3.33 (2H, m), 3.00 (1H, dd), 1.53 (3H, s), 1.31 (3H, s).

Compound #26 (±)-Trans-3-(3-ethoxycarbonyl-propylsulfanyl)-7-hydroxy-1,1-dimethyl-1,2,3,4-tetrahydro-naphthalen-2-yl-ammonium chloride

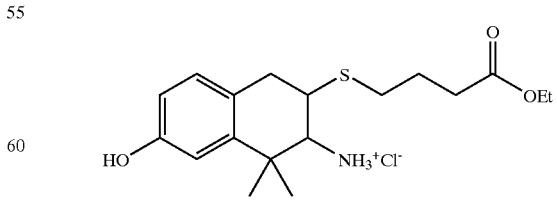

¹H NMR (400 MHz) (CDCl₃; d; ppm): 6.91 (1H, m), 6.80 (1H, m), 6.62 (1H, m), 4.14 (2H, m), 3.23 (1H, m), 3.14 (1H, m), 2.98 (1H, m), 2.77 (2H, m), 2.51 (2H, m), 1.96 (2H, m) 1.52 (3H, s), 1.30 (3H, s), 1.26 (3H, t, J=7.1 Hz).

Compound #27 (±)-Trans-3-benzenesulfonylmethylsulfanyl-7-hydroxy-1,1-dimethyl-1,2,3,4-tetrahydro-naphthalen-2-yl-ammonium chloride

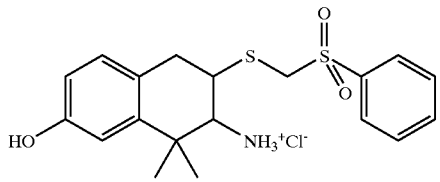

¹H NMR (400 MHz) (CD₃OD; d; ppm): 8.03 (2H, m), 7.80 (1H, m), 7.70 (2H, m), 6.88 (1H, d), 6.80 (1H, d), 6.64 (1H, dd), 4.56 (2H, s), 3.48 (2H, m), 3.21 (1H, m), 2.95 (1H, m), 1.53 (3H, s), 1.32 (3H, s).

Compound #28 (±)-Trans-7-hydroxy-1,1-dimethyl-trans-3-styrylsulfanyl-1,2,3,4-tetrahydro-naphthalen-2-yl-ammonium chloride

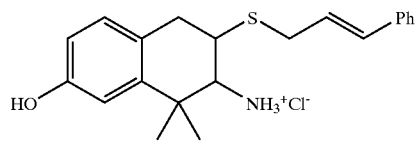

¹H NMR (400 MHz) (CD₃OD; d; ppm): 7.39 (2H, m), 7.30 (2H, m), 7.23 (1H, m), 6.88 (1H, d), 6.78 (1H, s), 6.60 (2H, m), 6.34 (1H, m), 3.59(2H, d), 3.38 (1H, m), 3.27 (1H, m), 3.16 (1H, m), 3.00 (1H, m), 1.51 (3H, s), 1.28 (3H, s).

Compound #29 (±)-Trans-7-hydroxy-TRANS-3-isobutylsulfanyl-1,1-dimethyl-1,2,3,4-tetrahydro-naphthalen-2-yl-ammonium chloride

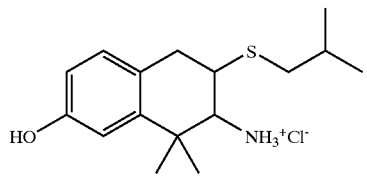

¹H NMR (400 MHz) (CD₃OD; d; ppm): 6.91 (1H, d), 6.79 (1H, d), 6.62 (1H, dd), 3.30 (1H, m), 3.23 (1H, dd), 3.10 (1H, m), 2.97 (1H, dd), 2.64 (2H, m), 1.88 (1H, m), 1.52 (3H, s), 1.29 (3H, s), 1.06 (6H).

Compound #30 (±)-Trans-7-hydroxy-1,1-dimethyl-trans-3-(2-phenoxy-ethylsulfanyl)-1,2,3,4-tetrahydro-naphthalen-2-yl-ammonium chloride

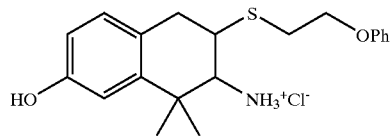

¹H NMR (400 MHz) (CD₃OD; d; ppm): 7.28 (2H, m), 6.89–6.97 (4H, m), 6.80 (1H, d), 6.63 (1H, dd), 4.27 (2H, m), 3.27–3.49 (3H, m), 3.15 (2H, m), 3.02 (1H, dd), 1.30 (3H, s,), 1.26 (3H, s).

Compound #31 (±)-Trans-1,1-diethyl-7-hydroxy-trans-3-(2-phenoxy-ethylsulfanyl)-1,2,3,4-tetrahydro-naphthalen-2-yl-ammonium chloride

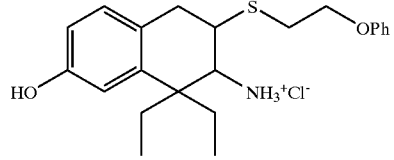

¹H NMR (400 MHz) (CD₃OD; d; ppm): 7.26 (2H, m), 6.91 (4H, m), 6.67 (2H, m), 4.27 (2H, m), 3.53 (1H, m), 3.45 (1H, m), 3.37 (1H, dd, J₁=5.3 Hz, J₂=16.5 Hz), 3.15 (2H, m), 2.93 (1H, dd, J₁=11.2 Hz, J₂=16.0 Hz), 2.08 (1H, m), 1.75 (2H, m), 1.66 (1H, m), 0.81 (3H, t, J=7.3 Hz), 0.69 (3H, t, J=7.0 Hz).

Compound #34 (±)-Trans-7-amino-6-(4-bromo-phenylsulfanyl)-8,8-dimethyl-5,6,7,8-tetrahydronaphthalen-2-ol hydrochloride

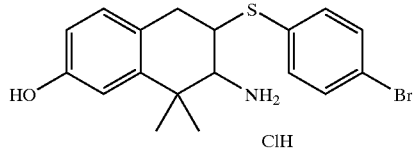

¹H NMR (400 MHz) (CD₃OD; d; ppm): 7.54(m, 4H), 6.8(m, 2H), 6.6(m, 1H), 3.57(m, 1H), 3.40(d, 1H, J=12 Hz), 3.14(dd, 1H, J=5.3 Hz, J=16 Hz), 2.86(dd, 1H, J=11 Hz, 5 Hz), 1.53(s, 3H), 1.32(s, 3H).

Compound #35 (±)-Trans-7-amino-8,8-dimethyl-6-(naphthalen-2-ylsulfanyl)-5,6,7,8-tetrahydro-naphthalen-2-ol

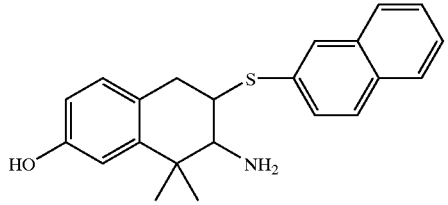

¹H NMR (400 MHz) (DMSO; d; ppm): 9.10(s, 1H), 8.04(d, 1H, J=1.3 Hz), 7.88(m, 3H), 7.59(dd, 1H, J=1.8 Hz, J=3 Hz), 7.50(m, 2H), 6.7(m, 2H), 6.45(m, 1H), 3.57(1H), 3.00(1H), 2.72(m, 2H), 1.98(br, 2H), 1.33(s, 3H), 1.13(s, 3H).

Compound #36 (±)-Trans-7-amino-6-(4-hydroxyphenylsulfanyl)-8,8-diamino-5,6,7,8-tetrahydro-naphthalen-2-ol hydrochloride

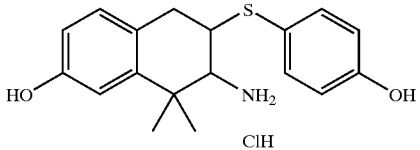

¹H NMR (400 MHz) (CD₃OD; d; ppm): 7.49(m, 2H), 6.82(m, 4H), 6.58(m, 1H), 3.3(m, 2H), 3.05(dd, 1H, J=5 Hz, J=8 Hz), 2.75(dd, 1H, J=9 Hz, J=5 Hz), 1.49(s, 3H), 1.29(s, 3H).

Compound #37 (±)-Trans-7-amino-6-(4-amino-phenylsulfanyl)-8,8-dimethyl-5,6,7,8-tetrahydro-naphthalen-2-ol dihydrochloride

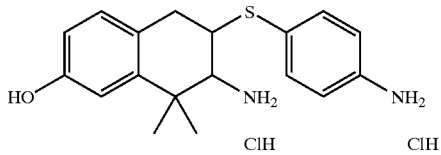

$^1$H NMR (400 MHz) (CD$_3$OD; d; ppm): 7.75(m, 2H), 7.38(m, 2H), 6.81(m, 2H), 6.61(m, 1H), 3.61(m, 1H), 3.43 (d, 1H, J=12 Hz), 3.11(dd, 1H, J=11 Hz, J=5.2 Hz), 2.87(dd, 1H, J=11 Hz, J=5 Hz), 1.54(s, 3H), 1.34(s, 3H).

Compound #38 (±)-Trans-7-amino-6-(3-hydroxy-phenylsulfanyl)-8,8-dimethyl-5,6,7,8-tetrahydro-naphthalen-2-ol

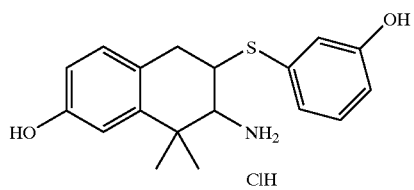

$^1$H NMR (400 MHz) (CD$_3$OD; d; ppm): 7.21(m, 1H), 7.04(m, 2H), 6.81(m, 3H), 6.60(m, 1H), 3.56(m, 1H), 3.40 (m, 1H), 3.14(dd, 1H, J=6 Hz, J=11 Hz), 2.86(dd, 1H, J=11 Hz, J=5 Hz), 1.52(s, 3H), 1.31(s, 3H).

Compound #39 (±)-Trans-3-(3-Aamino-6-hydroxy-4,4-dimethyl-1,2,3,4-tetrahydro-naphthalen-2-ylsulfanyl)-propionic acid ethyl ester hydrochloride

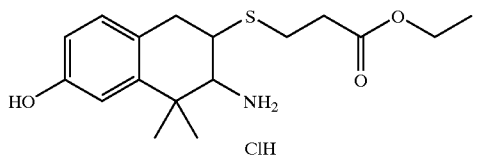

$^1$H NMR (400 MHz) (CD$_3$OD; d; ppm): 6.92(d, 1H, J=8.4 Hz), 6.80(d, 1H, J=2.3 Hz), 4.19(q, 2H, J=7 Hz, J=7 Hz), 3.42(d, 1H, J=11 Hz), 3.28(m, 2H), 2.98(m, 3H), 2.73(m, 2H), 1.52(s, 3H), 1.30(m, 6H).

Compound #40 (±)-Trans-7-amino-8,8-dimethyl6-phenethylsulfanyl-5,6,7,8-tetrahydro-naphthalen-2-ol hydrochloride;

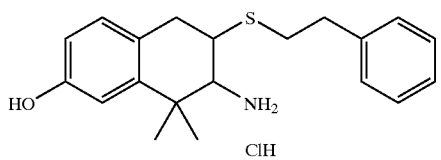

$^1$H NMR (400 MHz) (CD$_3$OD; d; ppm): 7.29(m, 4H), 7.23(m, 1H), 6.88(m, 1H), 6.78(m, 1H), 6.61(m, 1H), 3.18 (m, 2H), 3.06(m, 6H), 1.49(s, 3H), 1.27(s, 3H).

Compound #41 (±)-Trans-2-(3-amino-6-hydroxy4,4-dimethyl1,2,3,4-tetrahydronaphthalen-2-ylsulfanyl)-propionamide hydrochloride:

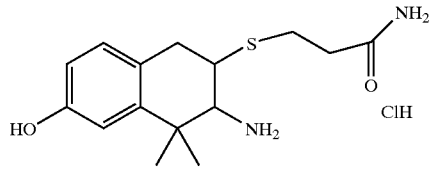

$^1$H NMR (400 MHz) (CD$_3$OD; d; ppm): 6.89(m, 1H), 6.82(m, 1H), 6.63(m, 1H), 3.45(m, 1H), 3.2(m, 3H), 2.85(m, 2H), 2.7(m, 1H), 2.55(m, 1H), 1.5(s, 3H), 1.3(s, 3H).

Compound #42 (±)-Trans-3-(3-amino-6-hydroxy-4,4-dimethyl-1,2,3,4-tetrahydro-naphthalen-2-ylsulfanyl)-propionic acid trifluoroacetate:

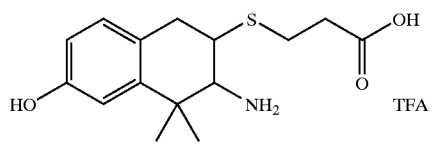

$^1$H NMR (400 MHz) (CD$_3$OD; d; ppm): 6.9(m, 1H), 6.78(m, 1H), 6.62(m, 1H), 3.45(d, 1H, J=11 Hz), 3.21(m, 2H), 2.98(m, 3H), 2.70(m, 2H), 1.53(s, 3H), 1.30(s, 3H).

Compound #43 (±)-Trans-3-{2-[1-carbamoyl-2-(4-hydroxy-phenyl)ethylcarbamoyl]-ethylsulfanyl}-7-hydroxy-1,1-dimethyl-1,2,3,4-tetrahydro-naphthalen-2-yl-ammonium; chloride:

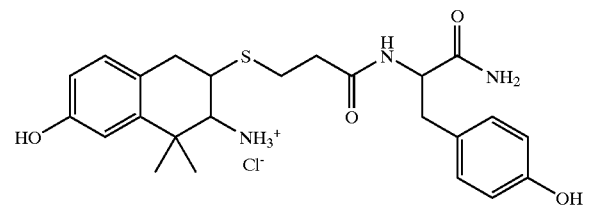

$^1$H NMR (400 MHz) (DMSO; d; ppm): 9.2(br, 1H), 8.0(br, 2H), 6.9(m, 1H), 6.8(m, 1H), 6.65(m, 2H), 6.6(m, 1H), 6.5(m, 2H), 3.3–2.8(m, 11H), 1.45(s, 3H), 1.3(s, 1H).

Compound #44 3-trans-(2-ethoxycarbonylethylsulfanyl)-1,1-diethyl-7-hydroxy-1,2,3,4-tetrahydro-naphthalen-2-yl-ammonium; chloride:

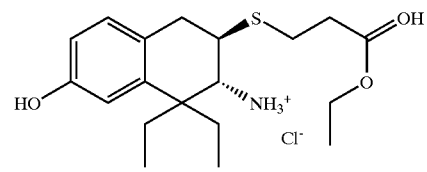

NMR($^1$H, MeOD): δ=6.95(m, 1H), 6.7(m, 1H), 6.6(m, 1H), 4.2(m, 2H), 3.2(m, 2H), 2.95(m, 2H), 2.85(m, 1H), 2.65(m, 2H), 1.95(m, 1H), 1.8(m, 2H), 1.65(m, 1H), 1.3(m, 3H), 0.75(m, 3H), 0.65(m, 3H) ppm.

Compound #45 3-trans-(2-carboxy-ethylsulfanyl)-1,1-diethyl-7-hydroxy-1,2,3,4-tetrahydro-naphthalen-2-yl-ammonium; chloride

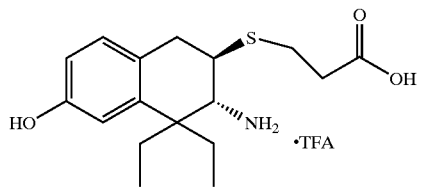

$^1$H NMR (CD$_3$OD) δ6.98 (d, 1H, J 8 Hz), 6.67–6.70 (m, 2H), 3.52 (d, 2H, J 11 ), 3.27–3.41 (m, 3H), 2.92–2.99 (m, 2H), 2.67–2.75 (m, 2H), 2.10–2.16 (m, 1H), 1.62–1.79 (m, 3H), 0.83 (m, 3H, J 8 Hz), 0.72 (m, 3H, J 8 Hz)

BIOLOGICAL ASSAYS

A. Receptor Affinity—Radioligand Binding Assay

Affinity for μ opioid receptor was assessed in vitro using radioligand binding assay employing rat brain membrane preparations as described in Schiller et al., Biophys. Res. Commun., 85, p.1322 (1975) incorporated herein by reference. Male Sprague-Dawley rats weighing between 350–450 g were sacrificed by inhalation of CO2. The rats were decapitated and the brains minus cerebellum were removed and place in ice-cold saline solution and then homogenized in ice-cold 50 mM Tris buffer pH 7.4 (10 ml/brain). The membranes were centrifuged at 14000 rpm for 30 min. at 4° C. The pellets were re-suspended in approximately 6 ml/brain of ice-cold Tris buffer 50 mM pH 7.4 and stored at −78° C. until ready for use. Protein quantification of the brain homogenate was conducted according to protein assay kit purchased (Bio-Rad).

(3H)-DAMGO was used as radioligands for the μ receptor. Radioligand 50 μl, membranes 100 μl and serially diluted test compound were incubated for 1 hr at room temperature or 22° C. Non specific binding was determined using 500 fold in the presence of tracer and membranes. Free ligand was separated from bound by filtration through Whatman GF/B paper (presoaked in polyethylenimine 1% aqueous solution) and rinsing with ice-cold 50 mM Tris pH 7.4 using a Brandel cell harvester. The filters were dried and radioactivity was counted in a 24 well microplate in the presence of 500 μl scintillant per well. Radioactivity was measured using a Wallac 1450 Microbeta counter. Inhibition constants (Ki) for the various compounds were determined from the IC50 according to the Cheng and Prusoff equation.

B. Central and Peripheral Analgesia—PBQ Writhing Assay

PBQ (phenyl-ρ-benzoquinone) induced writhing in mice was used to assess both central and peripheral analgesia of compounds of the invention according to the experimental protocol described in Sigmund et al., Proc. Soc. Exp. Biol. Med., 95, p. 729(1957) which is incorporated herein by reference. The test was performed on CD-1 male mice weighing between 18 and 22 g. The mice were weighed and marked and administered peritoneally with 0.3 ml/20 g by weight 0.02% solution of phenylbenzoquinone (PBQ). The number of writhings was counting 5 minutes after PBQ injection and for a period of 20 minutes. ED50 values (dose of compound which induced a 50% reduction in the number of writhes observed compared to the control) was calculated using non linear regression of dose response curve. The PBQ was injected at time intervals of 5, 20 or 30 minutes after intravenous, subcutaneous or oral administration respectively of the compound (or medium, or standard).

Aqueous solution of 0.02% PBQ was prepared by dissolving PBQ in 5% ethanol/saline 0.9% solution.

C. Central Analgesia Tail Flick Assay

The compounds of the present invention were evaluated for central analgesia as described in D'Amour et al. J.Pharmacol. 72:74–79, 1941 which is herein incorporated by reference. Male mice CD-1 were weighed and marked on their tail. Tail is placed between two light beams at specific intensity using a Tail Flick Analgesia Meter, Columbus Instrument. Each mouse was tested at specific time points after compound or saline injection and latency period was noted. Cut off latency was settled at 10 seconds. ED$_{50}$ value was calculated from results obtained for different doses at 5 minutes for intravenous injection and at 30 minutes for oral and subcutaneous injection using non linear regression analysis of the dose response curve.

TABLE 1

| Compound # | Ki$_μ$ |
|---|---|
| #1 | 1.1 |
| #2 | 286 |
| #3 | 0.11 |
| #4 | 0.61 |
| #5 | 0.6 |
| #6 | 11.6 |
| #7 | 0.9 |
| #8 | 6.5 |
| #9 | 1.9 |
| #10 | 3.7 |
| #11 | 45.3 |
| #12 | 0.59 |
| #13 | 0.6 |
| #14 | 81 |
| #15 | 0.28 |
| #16 | 9 |
| #17 | 30 |
| #18 | 8.1 |
| #19 | 6.2 |
| #20 | 48.8 |
| #21 | 1.11 |
| #22 | 0.23 |
| #23 | 69.2 |
| #24 | 0.32 |
| #25 | 39.4 |
| #26 | 7.2 |
| #27 | 64.3 |
| #28 | 22 |
| #29 | 28.6 |
| #30 | 2.3 |
| #31 | 0.89 |
| #32 | 0.33 |
| #33 | 0.9 |
| #34 | 0.44 |
| #35 | 1.25 |
| #36 | 0.73 |
| #37 | 1.4 |
| #38 | 1.3 |
| #39 | 0.37 |
| #40 | 1.96 |
| #41 | 3.4 |
| #42 | 96.5 |
| #43 | 7 |
| #44 | 0.18 |
| #45 | 3.06 |

While the invention has been described in connection with specific embodiments thereof, it will be understood that it is capable of further modifications and this application is intended to cover any variations, uses or adaptations of the invention following, in general, the principles of the invention and including such departures from the present description as come within known or customary practice within the art to which the invention pertains, and as may be applied to the essential features hereinbefore set forth, and as follows in the scope of the appended claims.

What is claimed is:
1. A compound represented by formula (1)

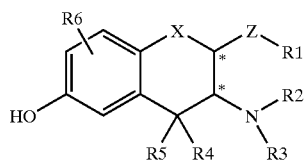

and pharmaceutically acceptable derivatives thereof;
wherein;

Z is S,

X is —CR$_7$R$_8$— wherein R$_7$ and R$_8$ are independently selected from the group consisting of H, OH, halogen, CN, COOH, CONH$_2$, amino, nitro, SH, C$_{1-6}$alkyl where one or more of the carbon atoms in said C$_{1-6}$alkyl may optionally be substituted by one or more heteroatoms selected from O, S and N, C$_{2-6}$ alkenyl where one or more of the carbon atoms in said C$_{2-6}$ alkenyl may optionally be substituted by one or more heteroatoms selected from O, S and N, C$_{2-6}$alkynyl where one or more of the carbon atoms in said C$_{2-6}$alkynyl may optionally be substituted by one or more heteroatoms selected from O, S and N; and COOR$_c$ wherein R$_c$ is C$_{1-6}$alkyl, C$_{2-6}$alkenyl or C$_{2-6}$alkynyl;

R$_1$ is selected from the group consisting of H, C$_{1-12}$alkyl where one or more of the carbon atoms may optionally be substituted by one or more heteroatoms selected from O, S and N, C$_{2-12}$alkenyl where one or more of the carbon atoms may optionally be substituted by one or more heteroatoms selected from O, S and N, C$_{2-12}$alkynyl where one or more of the carbon atoms may optionally be substituted by one or more heteroatoms selected from O, S and N, C$_{6-12}$ aryl, C$_{6-12}$ aralkyl, C$_{6-12}$ aryloxy, and C$_{1-2}$ acyl;

R$_2$ and R$_3$ are independently selected from the group consisting of C$_{1-6}$ alkyl where one or more of the carbon atoms may optionally be substituted by one or more heteroatoms selected from O, S and N, C$_{2-6}$alkenyl where one or more of the carbon atoms may optionally be substituted by one or more heteroatoms selected from O, S and N, C$_{2-6}$alkynyl where one or more of the carbon atoms may optionally be substituted by one or more heteroatoms selected from O, S and N, C$_{6-12}$ aryl, C$_{6-12}$ aralkyl, and H;

R$_4$ and R$_5$ are independently selected from the group consisting of C$_{1-6}$ alkyl where one or more of the carbon atoms may optionally be substituted by one or more heteroatoms selected from O, S and N, C$_{2-6}$alkenyl where one or more of the carbon atoms may optionally be substituted by one or more heteroatoms selected from O, S and N, C$_{2-6}$alkynyl where one or more of the carbon atoms may optionally be substituted by one or more heteroatoms selected from O, S and N, and H;

R$_6$ is hydrogen, OH, C$_{1-6}$ alkyl where one or more of the carbon atoms may optionally be substituted by one or more heteroatoms selected from O, S and N, C$_{2-6}$alkenyl where one or more of the carbon atoms may optionally be substituted by one or more heteroatoms selected from O, S and N, C$_{2-6}$alkynyl where one or more of the carbon atoms may optionally be substituted by one or more heteroatoms selected from O, S and N, O—C$_{1-6}$ alkyl where one or more of the carbon atoms may optionally be substituted by one or more heteroatoms selected from O, S and N, O—C$_{2-6}$alkenyl where one or more of the carbon atoms may optionally be substituted by one or more heteroatoms selected from O, S and N, O—C$_{2-6}$alkynyl where one or more of the carbon atoms may optionally be substituted by one or more heteroatoms selected from O, S and N, halogen, CN, COOH, CONH$_2$, amino, nitro, or SH;

with the provisos that:
1) not both R$_4$ and R$_5$ are H; and
2) at least one of R$_2$ and R$_3$ is H or C$_{1-6}$alkyl.

2. The compound of claim 1 wherein Z is S and X is —CH$_2$—.

3. The compound of claim 2 wherein the geometric relation between the substituents of carbons marked by an * is trans.

4. The compound of claim 3 wherein R$_2$ and R$_3$ are H.

5. The compound of claim 3 wherein R$_6$ is H.

6. The compound of claim 5 wherein R$_4$ and R$_5$ are C$_{1-4}$ alkyl.

7. The compound of claim 5 wherein R$_4$ and R$_5$ are independently selected from the group consisting of methyl, ethyl, isopropyl, propyl, butyl, and isobutyl.

8. The compound of claim 5 wherein and R$_5$ are ethyl.

9. The compound of claim 5 wherein R$_4$ and R$_5$ are methyl.

10. The compound of claim 5 wherein R$_1$ is selected from the group consisting of H, C$_{1-12}$alkyl, C$_{6-12}$ aryl, and C$_{6-12}$ aralkyl.

11. The compound of claim 5 wherein R$_1$ is selected from the group consisting of C$_{1-6}$ alkyl, C$_{6-12}$ aryl, and C$_{6-12}$ aralkyl.

12. The compound of claim 5 wherein R$_1$ is C$_{1-6}$ alkyl.

13. The compound of claim 5 wherein R$_1$ is selected from the group consisting of CH$_3$, —(CH$_2$)$_n$—CH$_3$, and —(CH$_2$)$_n$—O—CH$_3$ wherein n is an integer selected between 1 and 5.

14. The compound of claim 5 wherein R$_1$ is C$_{6-12}$ aryl.

15. The compound of claim 5 wherein R$_1$ is C$_{6-12}$ aralkyl.

16. A compound selected from the group consisting of:
Trans-7-Amino-8,8-dimethyl-6-methylsulfanyl-5,6,7,8-dihydro-naphthalen-2-ol, (compound #1);
Trans and cis-7-Amino-8,8-dimethyl-6-methylsulfanyl-5,6,7,8-dihydro-naphthalen-2-ol, (compound #2);
Trans-7-Amino-8,8-diethyl-6-methylsulfanyl-5,6,7,8-dihydro-naphthalen-2-ol, (compound #3);
Trans-7-Amino-8,8-dimethyl-6-phenylsulfanyl-5,6,7,8-tetrahydro-naphthalen-2-ol, (compound #4);
Trans-7-Amino-6-(3-amino-phenylsulfanyl)-8,8-dimethyl-5,66,7,8-tetrahydro-naphthalen-2-ol, (compound #7);
Trans-7-Amino-8,8-dimethyl-6-(4-methylsulfanyl-phenylsulfanyl)-5,6,7,8-tetrahydro-naphthalen-2-ol, (compound #8);
Trans-7-Amino-6-benzenesulfonylmethylsulfanyl-8,8-diethyl-5,6,7,8-tetrahydro-naphthalen-2-ol, (compound #9);
Trans-2-(3-Amino-4,4-diethyl-6-hydroxy-1,2,3,4-tetrahydro-naphthalen-2-ylsulfanyl)-acetamide (compound #10);
Trans-7-Amino-8,8-diethyl-6-(2-hydroxy-ethylsulfanyl)-5,6,7,8-tetrahydro-naphthalen-2-ol (compound 12);

Trans-7-Amino-6-(2-amino-ethylsulfanyl)-8,8-dimethyl-5,6,7,8-tetrahydro-naphthalen-2-ol (compound 14);

Trans-7-Amino-8,8-dimethyl-6-propylsulfanyl-5,6,7,8-tetrahydro-naphthalen-2-ol (compound 16);

Trans-7-Amino-6-isopropylsulfanyl-8,8-dimethyl-5,6,7,8-tetrahydro-naphthalen-2-ol (compound 17);

Trans-7-Amino-6-(2-hydroxy-ethylsulfanyl)-8,8-dimethyl-5,6,7,8-tetrahydro-naphthalen-2-ol (compound 18);

Trans-2-(3-Amino-6-hydroxy-4,4dimethyl-1,2,3,4-tetrahydro-naphthalen-2-ylsulfanyl)-acetamide (compound 19);

Trans-7-Dimethylamino-8,8-dimethyl-6-methylsulfanyl-5,6,7,8-tetrahydro-naphthalen-2-ol (compound 20);

8,8-dimethyl-trans-7-methylamino-6-methylsulfanyl-5,6,7,8-tetrahydro-naphthalen-2-ol (compound 21);

Trans-7-Amino-8,8-diethyl-6-phenylsulfanyl-5,6,7,8-tetrahydro-naphthalen-2-ol (compound 22);

8,8-dimethyl-trans-6-phenylsulfanyl-7-propylamino-5,6,7,8-tetrahydro-naphthalen-2-ol (compound 23);

Trans-7-Amino-6-(2-amino-phenylsulfanyl)-8,8-diethyl-5,6,7,8-tetrahydro-naphthalen-2-ol (compound 24);

Trans-7-Amino-8,8-dimethyl-6-(2,2,2-trifluoro-ethylsulfanyl)-5,6,7,8-tetrahydro-naphthalen-2-ol (compound 25);

Trans-4-(3-Amino-6-hydroxy-4,4-dimethyl-1,2,3,4-tetrahydro-naphthalen-2-ylsulfanyl)-butyric acid ethyl ester (compound 26);

Trans-7-Amino-6-benzenesulfonylmethylsulfanyl-8,8-dimethyl-5,6,7,8-tetrahydro-naphthalen-2-ol (compound 27);

Trans-7-Amino-8,8-dimethyl-6-(3-phenyl-allylsulfanyl)-5,6,7,8-tetrahydro-naphthalen-2-ol (compound 28);

Trans-7-Amino-6-isobutylsulfanyl-8,8-dimethyl-5,6,7,8-tetrahydro-naphthalen-2-ol (compound 29);

Trans-7-Amino-8,8-dimethyl-6-(2-phenoxy-ethylsulfanyl)-5,6,7,8-tetrahydro-naphthalen-2-ol (compound 30);

Trans-7-Amino-8,8-diethyl-6-(2-phenoxy-ethylsulfanyl)-5,6,7,8-tetrahydro-naphthalen-2-ol (compound 31);

(−)Trans-7-amino-8,8-dimethyl-6-methylsulfanyl-5,6,7,8-tetrahydro-naphthalen-2-ol (compound 32);

(+)Trans-7-amino-8,8-dimethyl-6-methylsulfanyl-5,6,7,8-tetrahydro-naphthalen-2-ol (compound 33);

Trans-7-amino-6-(4-bromo-phenylsulfanyl)-8,8-dimethyl-5,6,7,8-tetrahydro-naphthalen-2-ol (compound 34);

Trans-7-amino-8,8-dimethyl-6-(naphthalen-2-ylsulfanyl)-5,6,7,8-tetrahydro-naphthalen-2-ol (compound 35);

Trans-7-Amino-6-(4-hydroxy-phenylsulfanyl)-8,8-dimethyl-5,6,7,8-tetrahydro-naphthalen-2-ol (compound 36);

Trans-7-amino-6-(4-amino-phenylsulfanyl)-8,8-dimethyl-5,6,7,8-tetrahydro-naphthalen-2-ol (compound 37);

Trans-7-amino-6-(3-hydroxy-phenylsulfanyl)-8,8-dimethyl-5,6,7,8-tetrahydro-naphthalen-2-ol (compound 38);

Trans-3-(3-Amino-6-hydroxy-4,4-dimethyl-1,2,3,4-tetrahydro-naphthalen-2-ylsulfanyl)-propionic acid ethyl ester (compound 39);

Trans-7-amino-8,8-dimethyl-6-phenylsulfanyl-5,6,7,8-tetrahydro-naphthalen-2-ol (compound 40);

Trans-2-(3-amino-6-hydroxy-4,4-dimethyl-1,2,3,4-tetrahydro-naphthalen-2-ylsulfanyl)-propionamide (compound 41);

Trans-3-(3-amino-6-hydroxy-4,4-dimethyl-1,2,3,4-tetrahydro-naphthalen-2-ylsulfanyl)-propionic acid (compound 42);

Trans-2-[3-(3-Amino-6-hydroxy-4,4-dimethyl-1,2,3,4-tetrahydro-naphthalen-2-ylsulfanyl)-propionylamino]-3-(4-hydroxy-phenyl)-propionamide (compound 43);

3-trans-(2-ethoxycarbonyl-ethylsulfanyl)-1,1-diethyl-7-hydroxy-1,2,3,4-tetrahydro-naphthalen-2-yl (compound 44);

3-trans-(2-carboxy-ethylsulfanyl)-1,1-diethyl-7-hydroxy-1,2,3,4-tetrahydro-naphthalen-2-yl (compound 45);

and pharmaceutically acceptable derivatives thereof.

17. The compound of claim 16, wherein said compound is selected from the group consisting of: compound#1, compound#3, compound#4, compound#9, compound#31, compound#36, compound#37, compound#39, compound#41, compound#43, compound#44, and compound#45.

18. The compound of claim 17 wherein said compound is selected from the group consisting of compound#1, compound#3, compound#36, compound#44 and compound#45.

19. The compound of claim 17 wherein said compound is selected from the group consisting of compound#32 and compound#33.

20. A compound according to any one of claim 1–14, 15, or 16–18 wherein said compound is in the form of the (+) enantiomer, the (−) enantiomer and mixture of the (+) and (−) enantiomer including racemic mixture.

21. A compound according to any one of claim 1–14, 15, or 16–18 wherein said compound is in the form of the (+) enantiomer.

22. A compound according to any one of claim 1–14, 15, or 16–18 wherein said compound is in the form of the (−) enantiomer.

23. A pharmaceutical composition comprising a compound as defined in any one of claims 1–14, 16, or 16–18 and pharmaceutically acceptable carriers, diluents or adjuvants.

24. A method of treating pain in a mammal, wherein said pain is mediated at least in part by the $\mu$ opioid receptor, comprising administering to said mammal an analgesic amount of a compound as defined by any one of claim 1–14, 15, or 16–18.

* * * * *